United States Patent [19]

Huffman et al.

[11] Patent Number: 4,514,045
[45] Date of Patent: Apr. 30, 1985

[54] HELICHROMIC-SMECTIC LIQUID CRYSTAL COMPOSITIONS AND DISPLAY CELLS

[75] Inventors: William A. Huffman, Minneapolis; Harvey A. Brown, Lake Elmo, both of Minn.

[73] Assignee: Minnesota Mining and Manufacturing Company, Saint Paul, Minn.

[21] Appl. No.: 436,030

[22] Filed: Oct. 22, 1982

Related U.S. Application Data

[63] Continuation-in-part of Ser. No. 274,184, Jun. 22, 1981, Pat. No. 4,394,070, which is a continuation-in-part of Ser. No. 169,275, Jul. 16, 1980, abandoned.

[51] Int. Cl.$^3$ ............................ C09K 3/34; G02F 1/13
[52] U.S. Cl. .................................... 350/351; 252/299.1; 252/299.6; 252/299.68; 252/299.7; 350/349
[58] Field of Search ............... 252/299.1, 299.7, 299.6, 252/299.68, 299.01; 350/350, 351, 352, 349

[56] References Cited

U.S. PATENT DOCUMENTS

| | | | |
|---|---|---|---|
| Re. 28,806 | 5/1976 | Saeva et al. | 252/299.01 |
| 3,957,348 | 5/1976 | Saeva | 252/299.01 |
| 3,960,751 | 6/1976 | Moriyama et al. | 252/299.1 |
| 3,973,800 | 8/1976 | Tsukamoto et al. | 252/299.68 |
| 3,977,769 | 8/1976 | Tsukamoto et al. | 252/299.68 |
| 4,032,470 | 6/1977 | Bloom et al. | 252/299.1 |
| 4,105,299 | 8/1975 | Huffman et al. | 252/299.1 |
| 4,122,027 | 10/1978 | Cole, Jr. et al. | 252/299.1 |
| 4,137,193 | 1/1979 | Osman et al. | 252/299.1 |
| 4,143,947 | 3/1979 | Aftergut et al. | 252/299.1 |
| 4,145,114 | 3/1979 | Coates et al. | 252/299.1 |
| 4,153,343 | 5/1979 | Bloom et al. | 252/299.1 |
| 4,154,746 | 5/1979 | Huffman | 252/299.1 |
| 4,179,395 | 12/1979 | Cole, Jr. et al. | 252/299.1 |
| 4,196,974 | 4/1980 | Hareng et al. | 350/349 |
| 4,278,323 | 7/1981 | Mukoh et al. | 252/299.1 |
| 4,279,152 | 7/1981 | Crossland | 252/299.1 |
| 4,281,903 | 8/1981 | Gharadjedaghi | 252/299.1 |
| 4,291,948 | 9/1981 | Crossland et al. | 350/340 |
| 4,299,720 | 11/1981 | Osman et al. | 252/299.1 |
| 4,391,492 | 7/1983 | Lu et al. | 350/351 |
| 4,394,070 | 7/1983 | Brown et al. | 252/299.1 X |

FOREIGN PATENT DOCUMENTS

| | | | |
|---|---|---|---|
| 2104 | 5/1979 | European Pat. Off. | 252/299.1 |
| 26004 | 4/1981 | European Pat. Off. | 252/299.1 |
| 44666 | 7/1981 | European Pat. Off. | 252/299.68 |
| 2920730 | 11/1979 | Fed. Rep. of Germany | 252/299.1 |
| 50-157272 | 12/1975 | Japan | 252/299.68 |
| 51-22681 | 2/1976 | Japan | 252/299.68 |
| 55-25005 | 2/1980 | Japan | 252/299.1 |
| 1549584 | 8/1979 | United Kingdom | 252/299.1 |
| 1556311 | 11/1979 | United Kingdom | 252/299.1 |
| 2037803 | 7/1980 | United Kingdom | 252/299.1 |
| 2091753 | 8/1982 | United Kingdom | 252/299.1 |

OTHER PUBLICATIONS

Urabe, et al., J. Appl. Phys., 54(3), Mar. (1983), pp. 1552–1558.
Tani, et al., Appl. Phys. Lett., 33(4), Aug. 15, 1978, pp. 275–277.
Tsukamoto, et al., Jap. J. App. Phys., vol. 14, No. 9, pp. 1307–1312, (1975).
Cox, Mol. Cryst. Liq. Cryst., vol. 55, pp. 1–32, (1979).
Bloom, et al., Mol. Cryst. Liq. Cryst., vol. 40, pp. 213–221, (1977).
Bloom, et al., Mol. Cryst. Liq. Cryst., vol. 41, pp. 1–4, (1977).

*Primary Examiner*—Teddy S. Gron
*Assistant Examiner*—Catherine S. Kilby
*Attorney, Agent, or Firm*—Donald M. Sell; James A. Smith; Jennie G. Boeder

[57] ABSTRACT

A composition for use in thermally-addressable liquid crystal display devices, comprising a smectic liquid crystal material and a helichromic compound possessing both a chromophoric moiety and an optically-active moiety. The helichromic compound is a circularly dichroic dye capable of propagating incident visible light in a circularly polarized manner so that all polarizations of the incident light are absorbed. The composition comprising the helichromic compound can be utilized in thermally-addressable liquid crystal display devices to provide a display which operates at lower voltages, with faster response times, and higher contrast ratios.

26 Claims, 4 Drawing Figures

HELICHROMIC-SMECTIC LIQUID CRYSTAL COMPOSITIONS AND DISPLAY CELLS

FIELD OF THE INVENTION

This application is a continuation-in-part of copending application Ser. No. 274,184, now U.S. Pat. No. 4,394,070 filed June 22, 1981, which is a continuation-in-part of copending application Ser. No. 169,275, filed July 16, 1980, now abandoned.

The present invention relates to smectic liquid crystal compositions and thermally-addressed smectic liquid crystal display devices. Unique "helichromic" compounds possessing circularly dichroic light propagating characteristics when used in guest-host combination with smectic liquid crystals are disclosed.

BACKGROUND OF THE INVENTION

It has long been known to use liquid crystals having a smectic phase in display devices which may be addressed by using infrared radiation (U.S. Pat. No. 3,796,999). The combination of infrared addressing with electrical stimulation to produce data storage devices having memory erase is also known as shown in U.S. Pat. No. 3,836,243. Several variations of this type of device have been disclosed which utilize a thermally induced smectic to nematic, or smectic to cholesteric phase shift (Kahn, et al.; *Performance and Characteristics of Smectic Liquid Crystal Storage Displays in Liquid Crystal Devices*, T. Kallard, Ed., Optosonic Press, 1973).

Recently, several new types of liquid crystal displays have been disclosed which utilize a pleochroic dye in guest-host arrangement with a liquid crystal host having a smectic to nematic mesophase. Such displays are disclosed in U.S. Pat. No. 4,196,974.

Still more recently, a particularly advantageous display known as a smectic-cholesteric display has been described in U.S. Ser. No. 251,247, filed Apr. 6, 1981. Briefly, this display comprises a typical transmissive or reflective liquid crystal display having appropriate front and back electrode patterns and featuring a smectic liquid crystal medium including at least one pleochroic dye of high order parameter and at least one cholesteric liquid crystal compound. The liquid crystal medium is thermally sensitive and has a transition between an upper thermal cholesteric state and a lower smectic phase. The device is operated by heating the medium to its upper thermal cholesteric state. The medium is then rapidly cooled while a portion of the mixture is addressed by the application of an electric field. A homeotropic light transmissive state is developed in the portions of the mixture which are addressed by the electric field, while a light absorbing state develops in the unaddressed portions of the mixture. The pleochroic dye in the portion of the mixture which is unaddressed, absorbs incident light passing through the medium; the liquid crystal medium acting as a vehicle to orient the pleochroic dye molecules into a light absorbing position. Electrodes are provided adjacent the liquid crystal medium, and heating electrodes are also provided to heat the medium to the upper cholesteric phase. By selective activation of the electrodes, information can be readily displayed.

Due to its operating mechanism, the smectic-cholesteric display does not require the use of auxiliary polarizers. However, the display has a number of inherent disadvantages. Significant amounts, e.g. 5-15% by weight, of the cholesteric liquid crystal and dichroic dye additives must be incorporated into the smectic liquid crystal medium. These "foreign" additives are typically chemically and/or photochemically unstable in liquid crystal display systems and their addition introduces a potential source of harmful decomposition products into the display. In addition, it is well known that liquid crystal systems comprising chemically dissimilar mixtures of liquid crystals have properties which vary nonlinearly and unpredictably with composition and temperature.

SUMMARY OF THE INVENTION

The present invention relates to helichromic-smectic liquid crystal displays which require no auxiliary polarizers, and which operate at lower voltages with faster response times than do smectic-cholesteric liquid crystal displays. Additionally, the helichromic-smectic liquid crystal displays have higher contrasts and require fewer additives for performance than do corresponding smectic-cholesteric devices. The superior performance of the helichromic-smectic displays of the invention is due to the use of helichromic compounds in admixture with smectic liquid crystals. More specifically, the helichromic compounds are organic, nonionic compounds which are soluble in smectic liquid crystal materials, and which comprise at least one chromophoric moiety and at least one optically active moiety. The helichromic compound is capable of being ordered by the smectic liquid crystal material and performs as a circularly dichroic dye when in admixture with smectic liquid crystals.

As used herein, the term "helichromic" refers to the described helichromic compounds, to liquid crystal compositions containing such compounds, and also to display devices containing the helichromic compounds of the invention.

Also as used in this application, the term "helichromic" refers to the circularly dichroic property of the helichromic compounds which enables liquid crystal mixtures in which effective amounts of the helichromic compounds are included to absorb a substantial portion of incident visible light by propagating the incident light through circularly polarized modes, so that all polarizations of the incident visible light are absorbed.

DETAILED DESCRIPTION OF THE INVENTION

Figure 1:
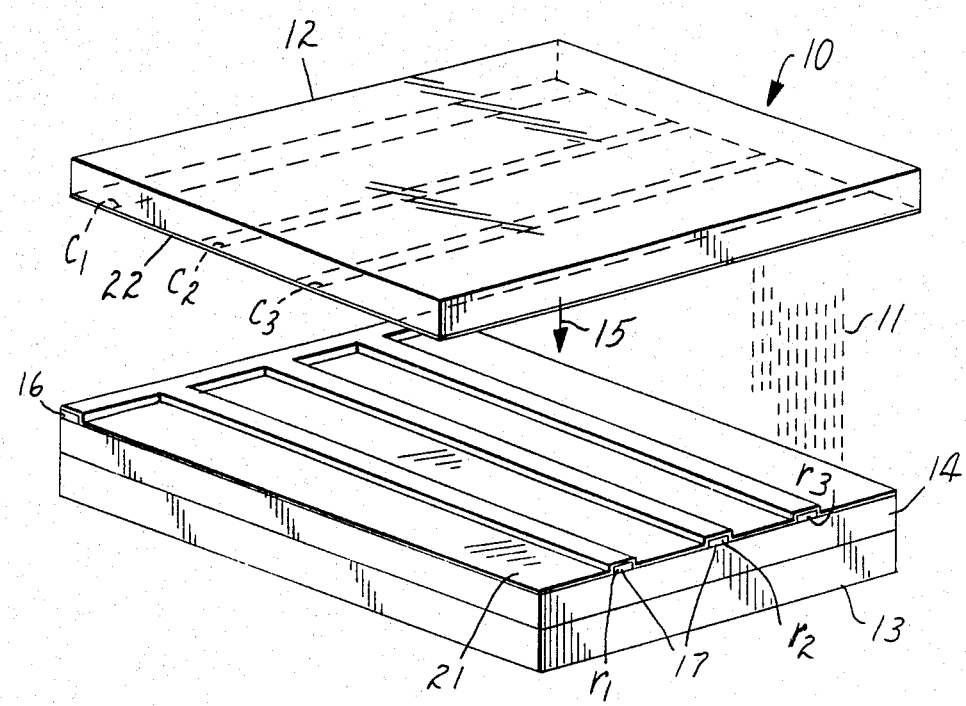
FIG. 1 is a perspective, exploded, schematic view of a helichromic-smectic liquid crystal display device made in accordance with the invention.

The helichromic-smectic displays of the present invention derive their superior performance properties from the use of helichromic compounds. The helichromic compounds are organic, nonionic compounds which are soluble in smectic liquid crystal compositions and which comprise at least one chromophoric moiety and at least one optically active moiety in a single molecule.

The chromophoric moieties or groups must be capable of absorbing at least some wavelength of incident electromagnetic radiation in the visible wavelengths. Useful chromophoric moieties or groups must also be capable of being joined with the optically active moieties and the resulting helichromic molecule must be circularly dichroic in nature. Useful chromophoric groups include the well-known azo, azo-stilbene, benzothiazolylpolyazo, azo-methine, methine, merocyanine, anthraquinone, methine-arylidene, tetrazine, oxadiazine, and carbazole-azo families of dyes.

Suitable optically active moieties or groups are those groups which enable mixtures of the helichromic compound and smectic liquid crystal materials to propagate incident visible light in a circularly polarized manner so that all polarizations of the incident light are absorbed. Normally the optically active or chiral group is an organic group having an asymmetric carbon atom. Preferred optically active groups include (+)-2-methyl and (+)-3-methyl alkyl groups, (+)-2-methyl and (+)-3-methyl alkoxy groups, (+)-citronellyl, (+)-camphanyl, (+)-3-methyl cyclohexyl, (+)-α-methyl benzyl, (+)-2-methyl butyl biphenyl, (+)-2-methyl butyl phenylthio, (+)-3-ethyl hexyl phenylbenzoate, (+)-2-methyl butyl methyl-2,3-dihydropermidine, (+)-3-methyl cyclopentyl-2,3-dihydropermidine, (+)-2-methyl cyclohexyl-2,3-dihydropermidine, (+)-α-phenethyl amine, (+)-N-2-methyl butyl aminonaphthalene and the like.

Preferred helichromic compounds of the present invention can be represented by the general formula Q—(Z)$_n$ wherein Q is the chromophoric group, Z is the optically active group and n is an integer having a value of one or more, and is preferably an integer from 1 to 4.

The number, n, of optically active groups, Z, which can be substituted on the chromophoric group, Q, is dependent on the number and position of reactive sites available on Q. For example, when Q is an azo, azo-stilbene, benzothiazolyl polyazo, merocyanine, azomethine, methine, methine-arylidene, tetrazine, oxadiazine, or carbazole-azo group, n is preferably 1 or 2 and the optically active group, Z, is substituted in a position along the long axis of Q so as not to significantly decrease the effectiveness of the helichromic compound as a circularly dichroic dye.

When Q is an anthraquinone-based group, the anthraquinone skeleton is normally substituted in one or more of the 1 through 8 positions independently with optically active groups. Preferably the optically active group or groups is substituted in 2,3, 6 and/or 7 positions independently, and any of the remaining positions may be occupied by small side groups or auxochromes which influence color absorption and solubility, such as F, Cl, Br, NO$_2$, NH$_2$, N(alk)$_2$, N=CH(alk), OH, CN, CF$_3$, SCN, CHO, and SH. Additionally, when the anthraquinone is substituted with two NH$_2$ groups in either the 1 and 4, or 5 and 8 positions, the 2 and 3, or 6 and 7, positions of the anthraquinone skeleton, respectively, may be substituted with a cyclic dicarboximide group having an optically active group attached to the nitrogen. Other ballasting or auxochromic groups which may affect the other parameter or absorption band of the chromophoric moiety are permitted substituents in the remainder of the available positions, as is known in the art.

The optically active moiety Z, may be linked to the chromophoric moiety Q by organic linking groups. Preferred linking groups include: —CH=N—, —CH=CH—, —N=N—, =C=C=, —NH—, —N(alk)—, —O—, —S—, —(CH$_2$)$_p$—, —C(CH$_3$)$_2$—,

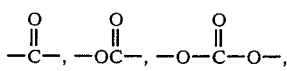

—C$_6$H$_{10}$—, phenyl, naphthyl, cyclic dicarboximide groups, and combinations thereof, wherein p is 1, 2, 3, 4, or 5.

The chromophoric moiety Q may be substituted in a number of available positions with one or more additional ballasting groups. Exemplary ballasting groups include NH$_2$, —(CH$_2$)$_p$—CH$_3$, —O—(CH$_2$)$_p$CH$_3$, —CH(CH$_3$)$_2$,

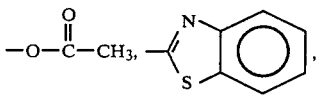

C$_6$H$_{11}$, phenyl groups, naphthyl groups, heterocyclic nitrogen, oxygen and sulfur-containing rings, and combinations thereof, wherein p is 0, 1, 2, 3, or 4. These ballasting groups may be linked to the chromophoric moiety Q with the linking groups described above.

In addition, Q may be substituted in any available position on any aromatic ring by small side groups or auxochromes which influence color absorption and solubility of the helichromic compound. Exemplary of such side groups are lower alkyl groups, lower alkoxy groups, F, Cl, Br, NO$_2$ NH$_2$(alk)$_2$, —N=CH(alk), OH, CN, CF$_3$, SCN,

SH, carbonyl and combinations thereof.

Exemplary helichromic compounds of the general formula

Q—(Z)$_n$ wherein Q is an azo group include the following:

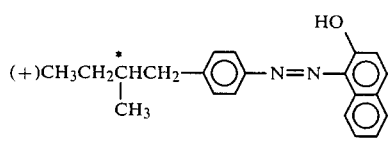

-continued
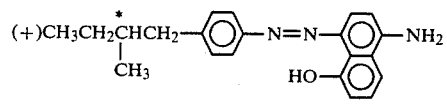
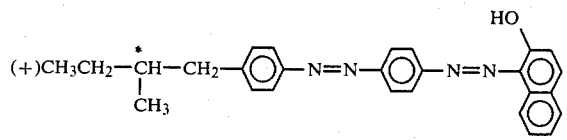
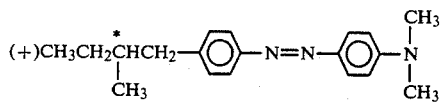
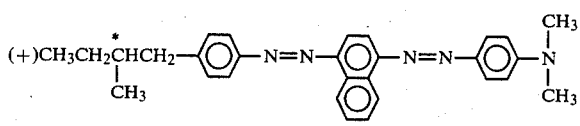
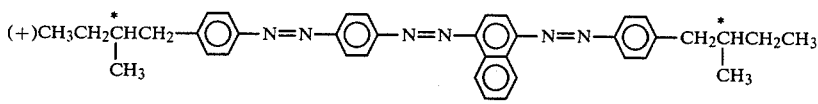
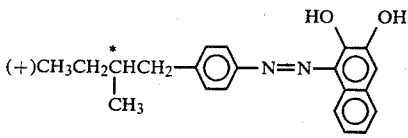
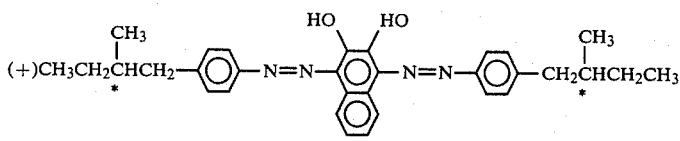
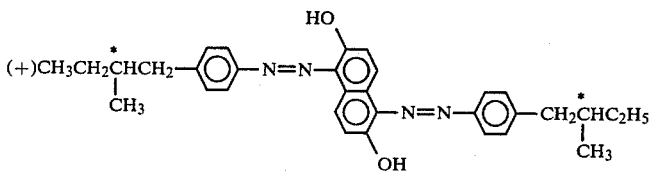
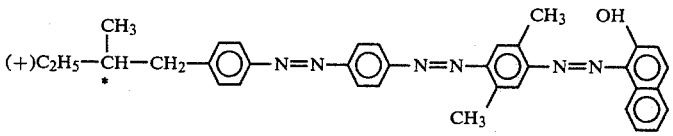
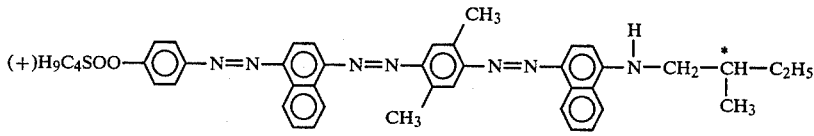
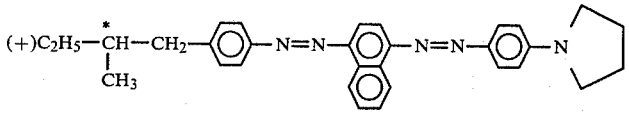
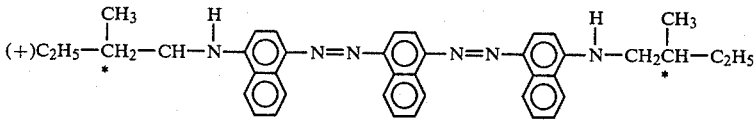

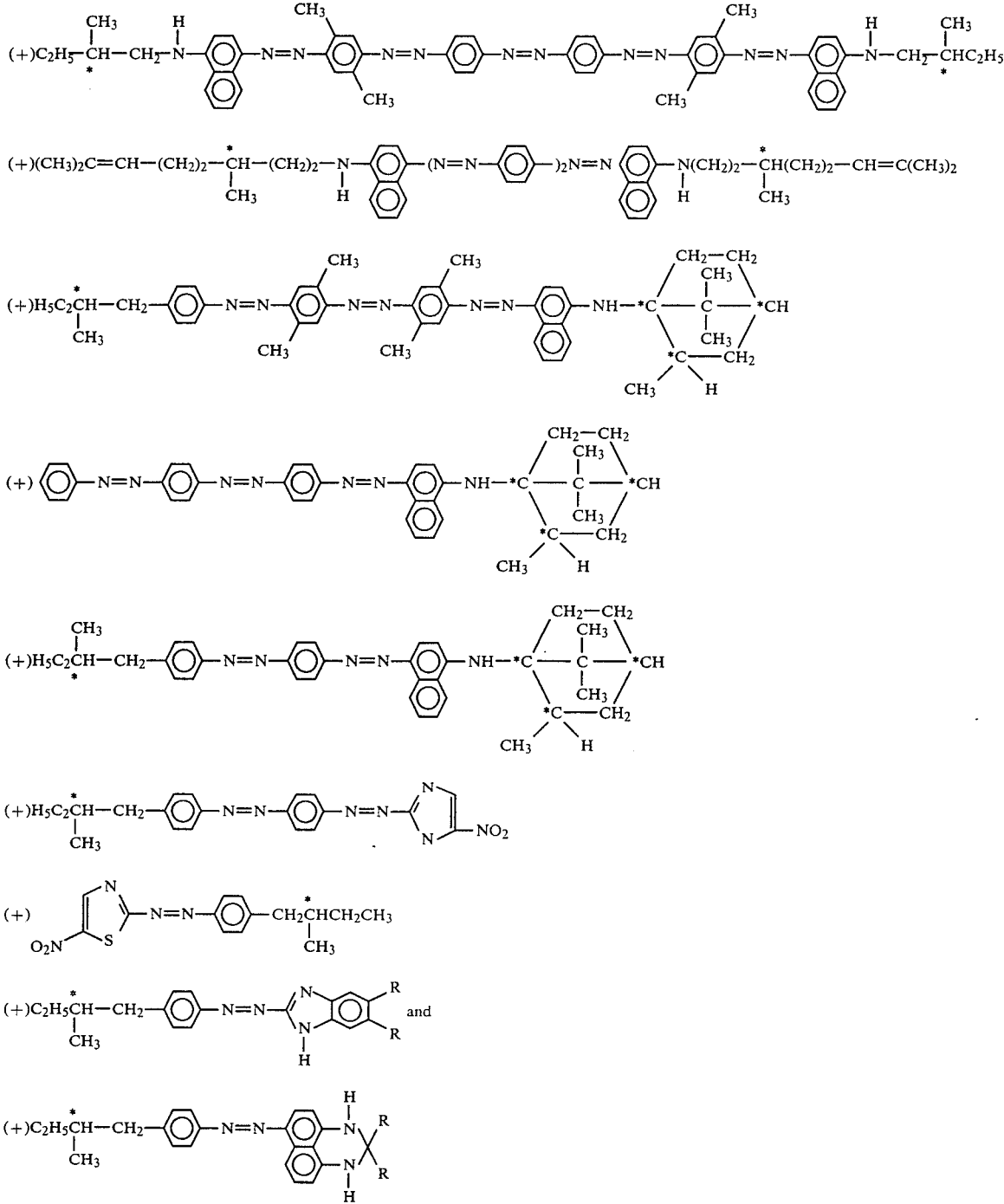
R = lower alkyl (C₁-C₄)
Exemplary helichromic compounds of the general formula
$$Q-(Z)_n$$
wherein Q is a benzothiazolylpolyazo group include the following:
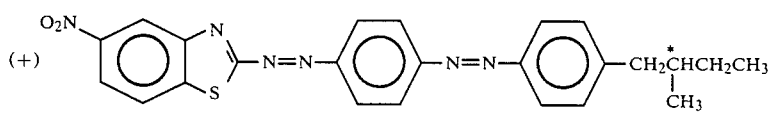

-continued
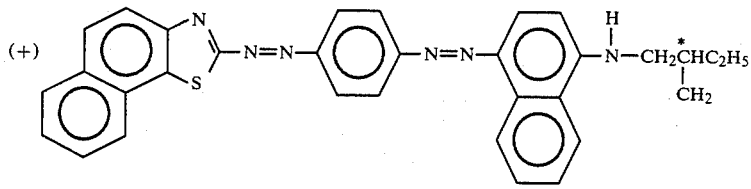
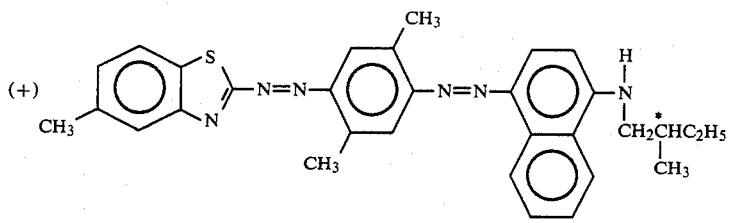
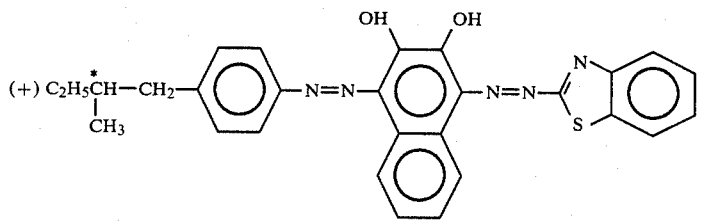
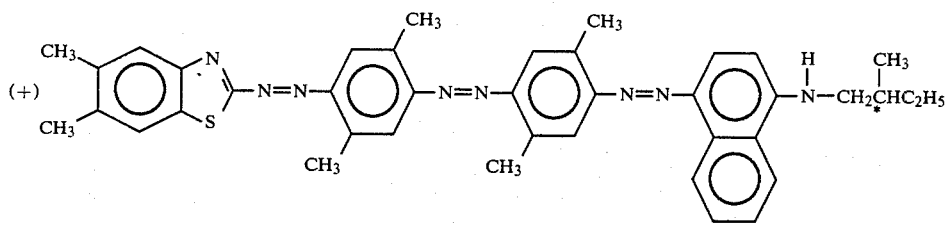
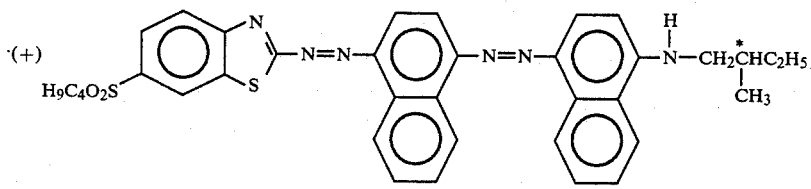
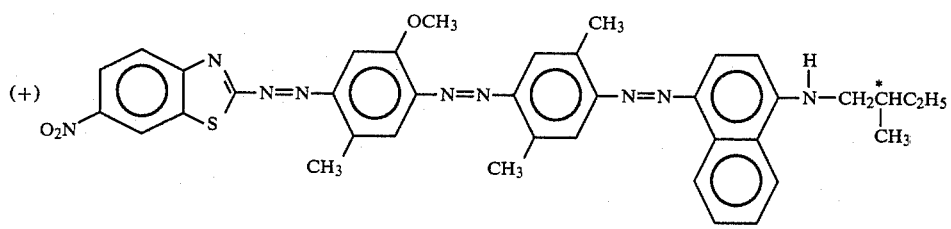
Exemplary helichromic compounds of the general formula
$$Q-(Z)_n$$
wherein Q is an azo-stilbene group include the following:
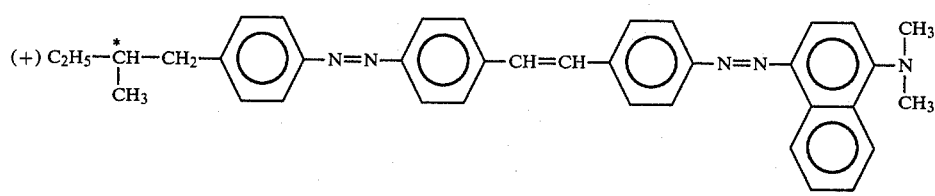

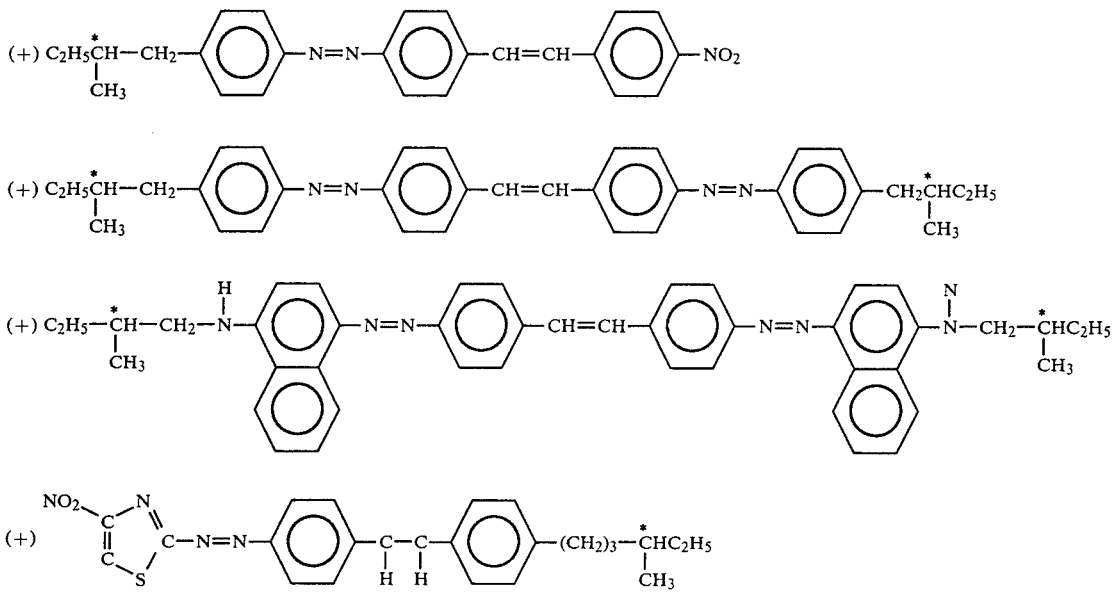
Exemplary helichromic compounds wherein Q is an azo-methine group include the following:
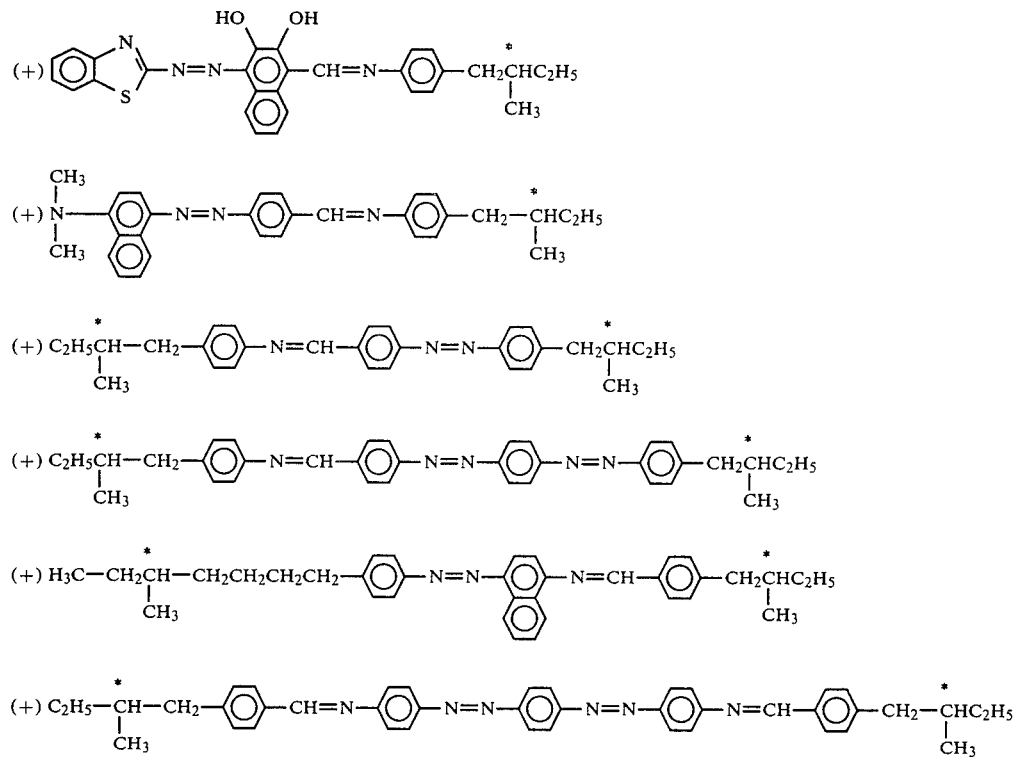
Exemplary helichromic compounds wherein Q is a methine group include the following:
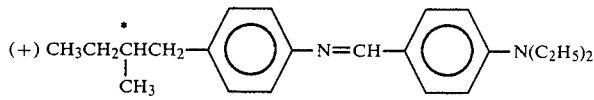

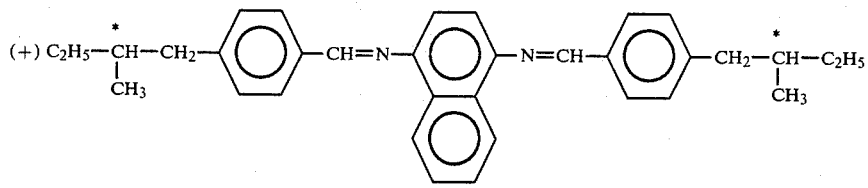
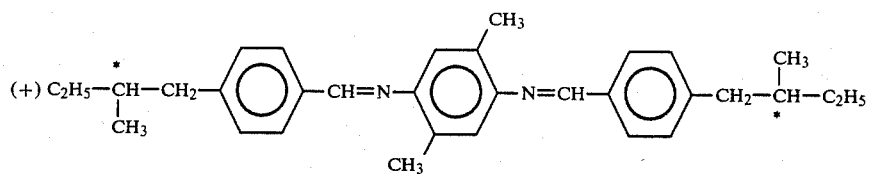
Exemplary helichromic compounds wherein Q is a methine-arylidene group include the following:
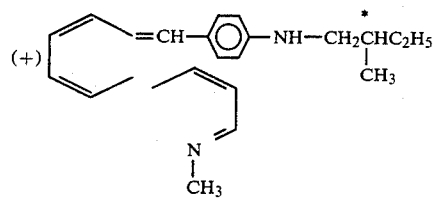
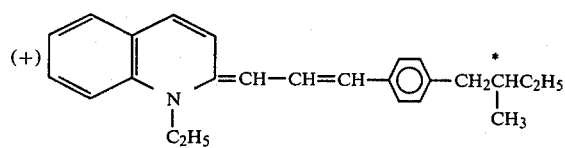
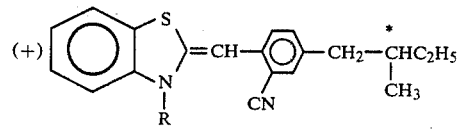
An exemplary helichromic compound wherein Q is a merocyanine group is the following:
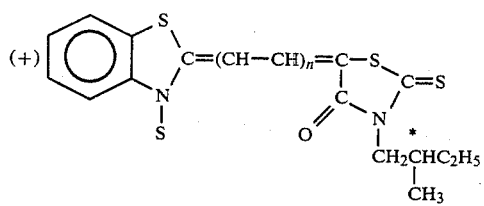
n = 1, 2 or 3.
Exemplary helichromic compounds wherein Q is an anthraquinone group include the following:
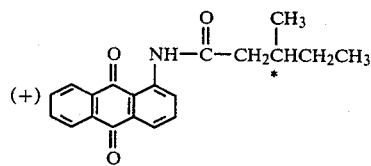
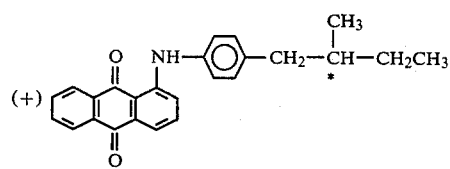
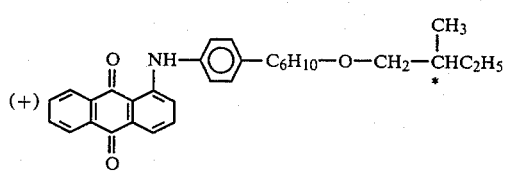
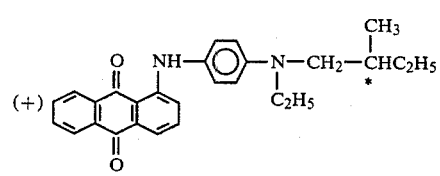
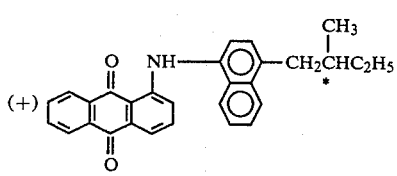
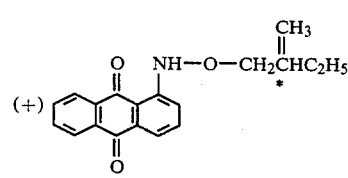

-continued
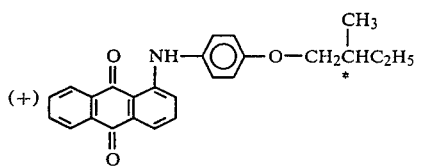
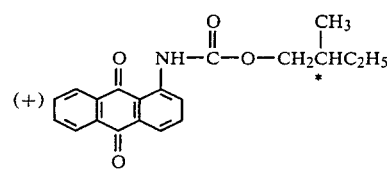
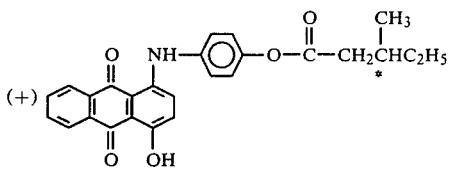
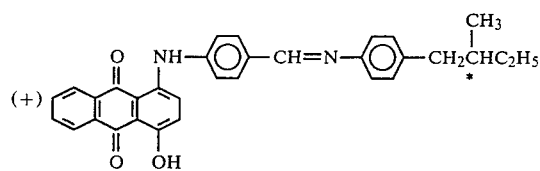
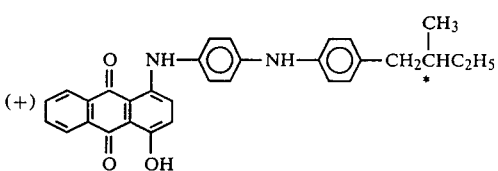
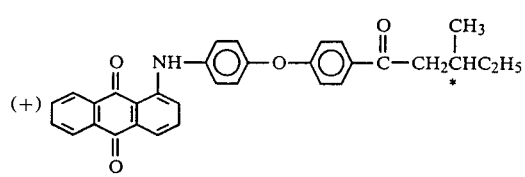
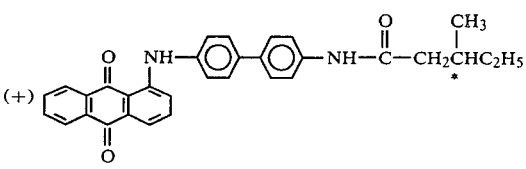
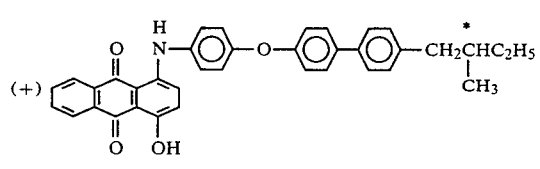
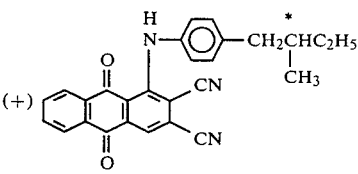
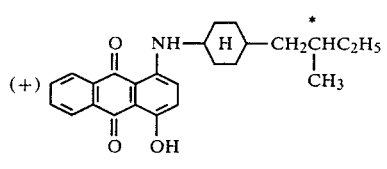
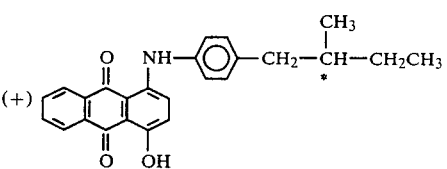
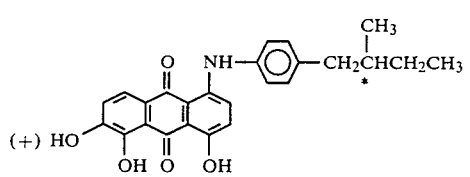
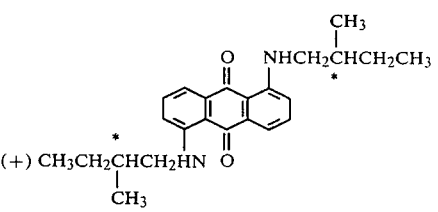
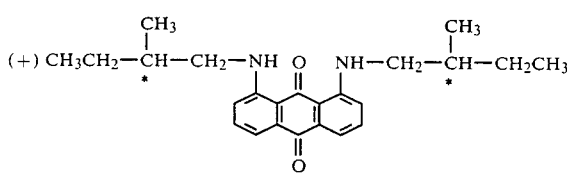

-continued
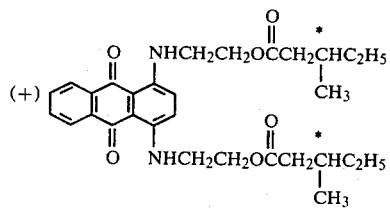
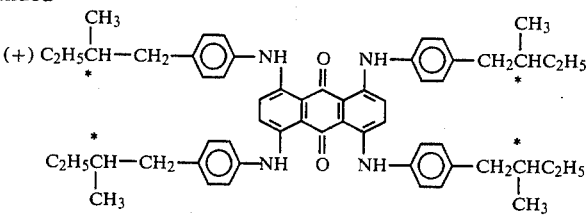
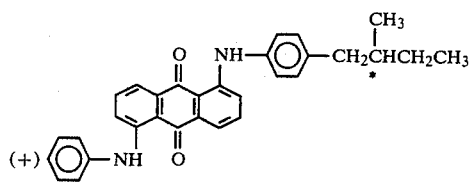
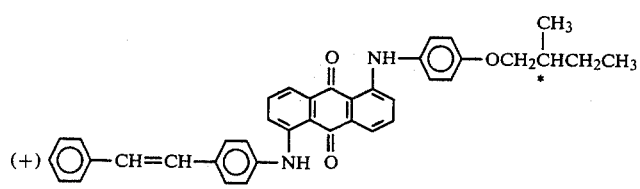
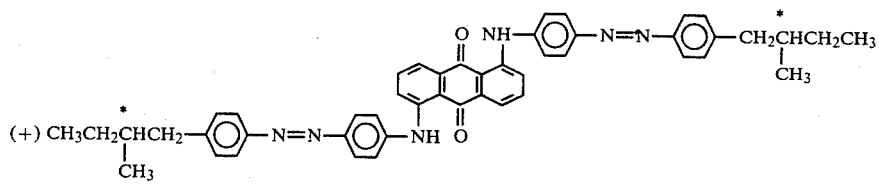
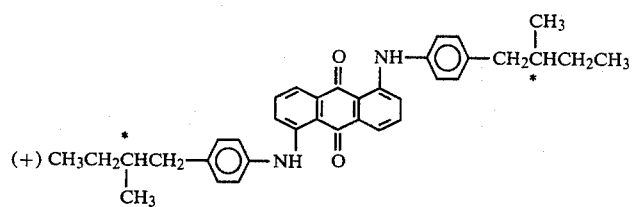
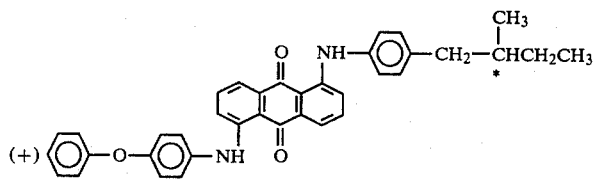
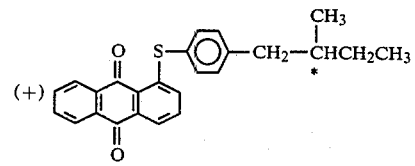
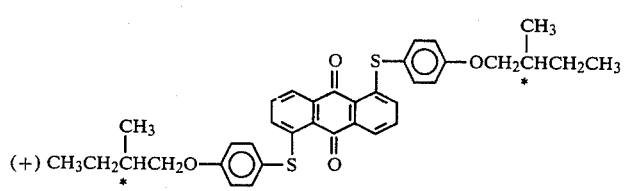
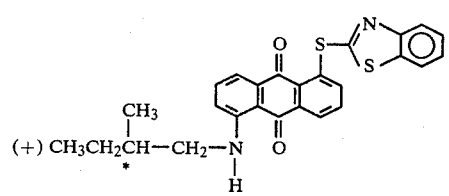
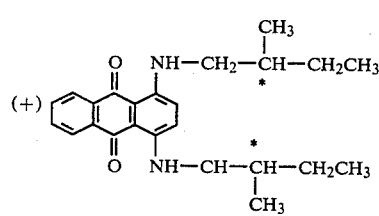
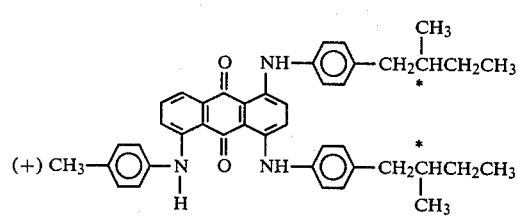

-continued
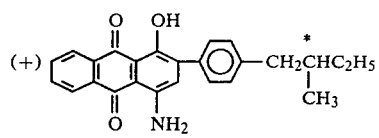
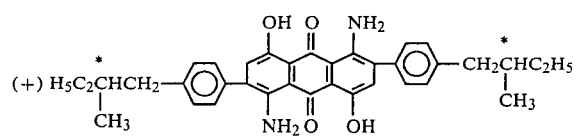
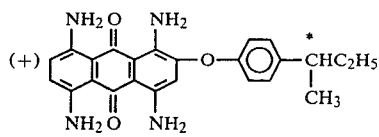
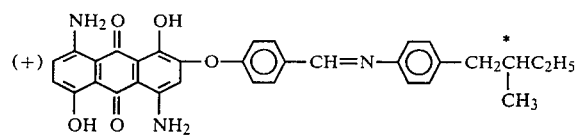
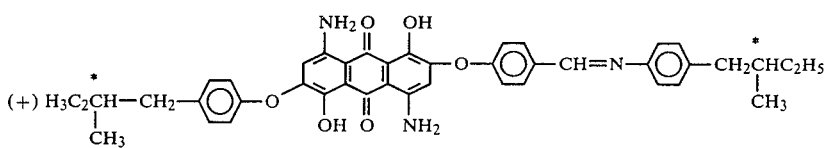
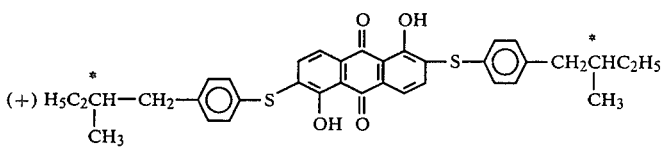
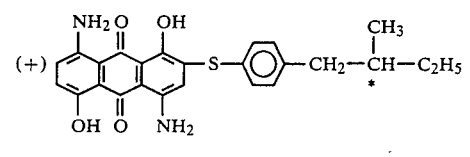
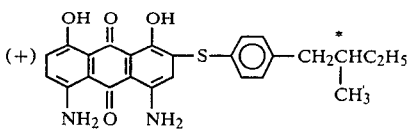
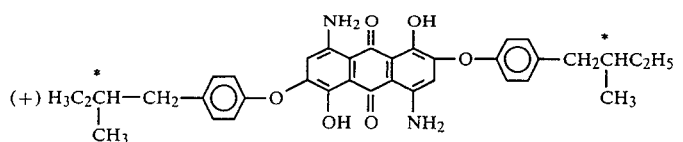
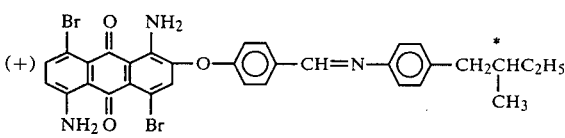
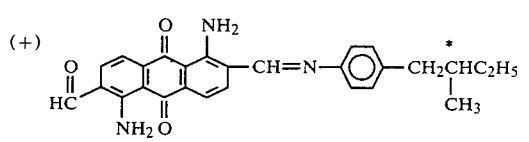
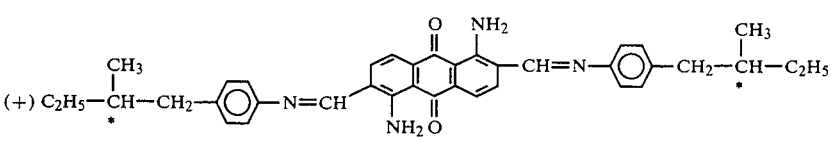
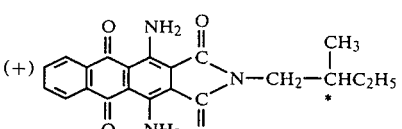
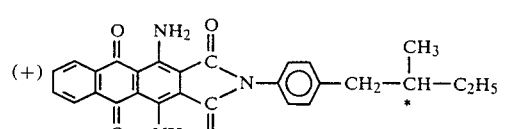

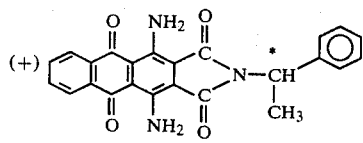

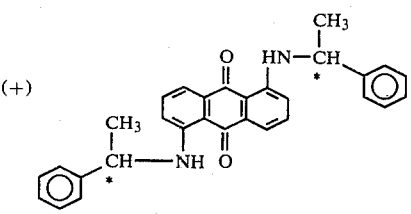

Preferred helichromic compounds wherein Q is a tetrazine group have the following general formula:

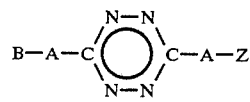

wherein Z is a helical ordering group as described hereinabove, A is independently selected from the group consisting of para-substituted aryl and para-substituted cyclohexyl groups, and combinations thereof, and B is selected from the group consisting of hydrogen, a lower alkyl or alkoxy, a heterocyclic oxygen-containing ring, Z, and combinations thereof. It is contemplated that linking groups, as desribed hereinabove, may be present between B and A, Z and A, and A and the rest of the molecule. Furthermore, additional ballasting groups and auxochromes may be present in available positions on the helichromic molecule, as described hereinabove.

Exemplary tetrazine-type helichromic compounds include the following:

Preferred helichromic compounds wherein Q is an oxadiazine group have one of the following general formulas:

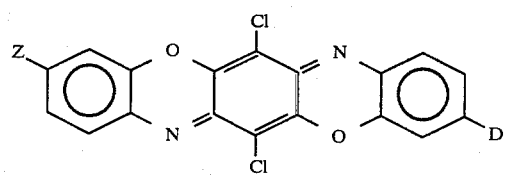

or

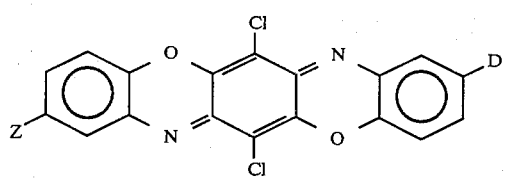

wherein Z is a helical ordering group as described hereinabove, and D is selected from the group consisting of hydrogen, a lower alkyl or alkoxy, aryl groups, Z, and

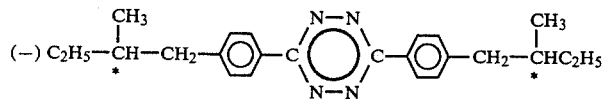

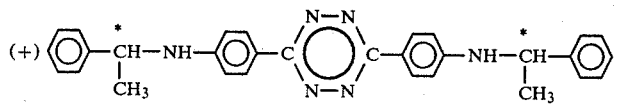

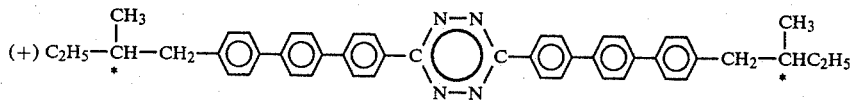

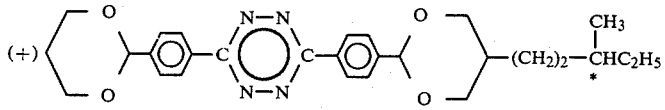

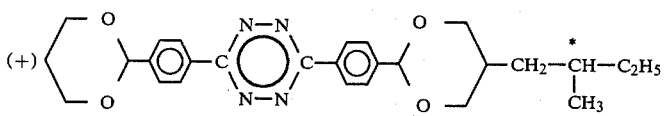

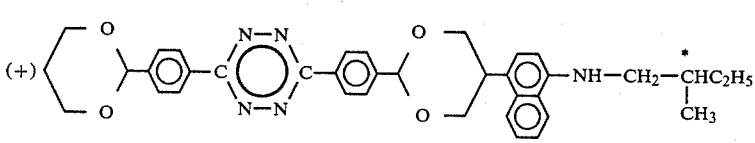

combinations thereof. It is contemplated that linking groups, as described hereinabove, may be present between any Z or D and the rest of the helichromic molecule. Furthermore, additional ballasting groups and auxochromes may be present in available positions on the helichromic molecule, as described hereinabove.

Exemplary helichromic compounds wherein Q is an oxadiazine group include the following:

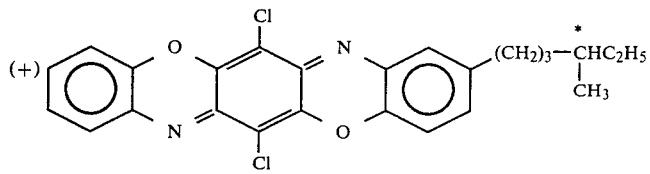

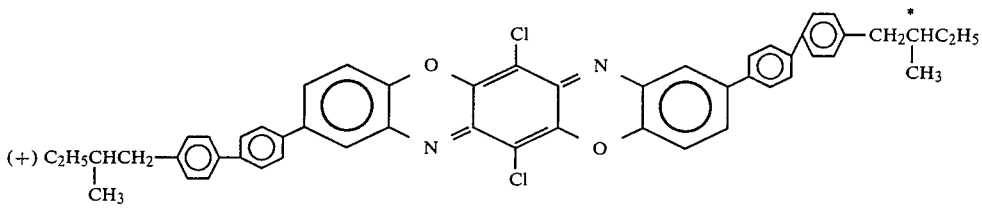

Preferred helichromic compounds wherein Q is a carbazole-azo group having the following general formula:

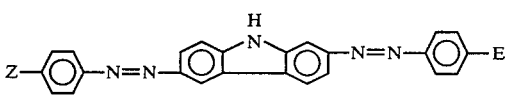

wherein Z is a helical ordering group as described hereinabove, and E is selected from the group consisting of hydrogen, and lower alkyl or alkoxy, and aryl group, Z, and combinations thereof. It is contemplated that linking groups, as described hereinabove, may be present between any Z or E and the rest of the helichromic molecule. Furthermore, additional ballasting groups and auxochromes may be present in available positions on the helichromic molecule, as described hereinabove.

Exemplary helichromic compounds wherein Q is a carbazole azo group include the following:

group, (+)-3-methyl butyl group, (+)-citronelly group, (+)-camphanyl group, (+)-3-methyl cyclohexyl group, or (+)-α-methyl benzyl group. However, other useful chiral anilines may have the optically-active group in the ortho or meta ring positions. Additional substituents, other than amino groups, may be present on the ring such as methyl, nitro, cyano, and hydroxy groups. The preparation of (+)-p-amino-2-methylbutylbenzene, i.e., (+) chiral aniline, is shown in D. Dolphin and Z. Muljiani, Journal of Chemical Physics, Vol. 58 [2], 414 (1973).

Alternatively the nitroso derivatives of the chiral aniline may be utilized to synthesize azo-type helichromic compounds by coupling with an amino compound.

Diazotization using alkali metal nitrite in mineral acid or using nitrosylsulfuric acid is also effective in the practice of the present invention, and those skilled in the art and science of synthetic chemistry will appreciate the various techniques involved.

Helichromic polyazo compounds may be synthesized by sequential diazotization and coupling. Reference is made to U.S. Pat. No. 4,145,114, for detailed procedures. Other pertinent references include U.S. Pat. Nos. 4,032,219; 4,029,392; 4,027,950; and 4,116,861.

Helichromic polyazo compounds may also be synthesized by tetraazotization of a polyaryl diamine and subsequent coupling with a chiral nitroso benzene group.

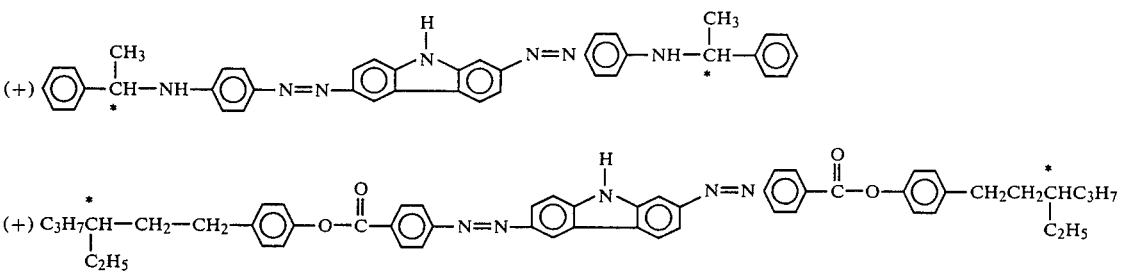

The helichromic azo and azo-stilbene compounds of this invention may be synthesized using methods of diazotization normally employed to synthesize other azo and azo-stilbene dyes. The literature abounds with methods of diazotization and specific organic synthetic procedures relating to diazotization and coupling reaction schemes. Helichromic azo and azo-stilbene type compounds may be synthesized by direct diazotization of the (+) chiral aniline. Preferred optically-active anilines have a para substituted (+)-2-methylbutyl Examples of useful polyaryl diamines include

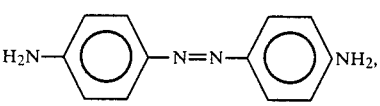

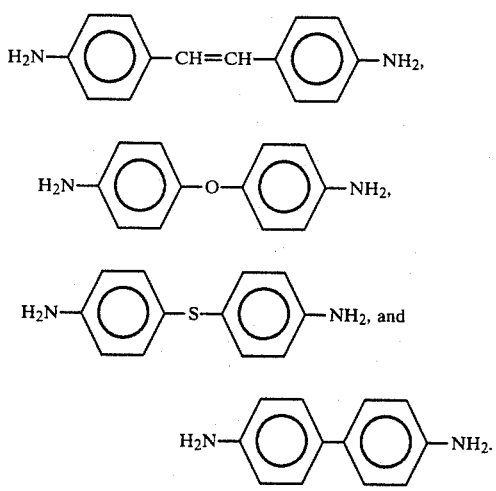

Helichromic polyazo compounds having more than one chiral group may be obtained by reacting a helichromic azo compound with a chiral nitroso compound, obtained by oxidation of the corresponding chiral aryl amine with Caros acid (the procedure is taught in Hickenbottom, *Organic Synthetic Chemistry*, Vol. II, p. 310 (1956)), in a minimum quantity of glacial acetic acid.

Helichromic benzothiazylpolyazo compounds may be obtained by converting benzothiazyl amines to the corresponding diazotate by the use of organic alkyl nitrites. The diazotate is then coupled to an aniline in weak acid and the benzothiazolyl azoaniline dye intermediate is recovered. Further diazotization and coupling to chiral anilines yields helichromic compounds. Particularly preferred benzothiazylpolyazo dye precursors are disclosed in Applicant's copending patent application U.S. Ser. No. 216,010.

Helichromic compounds of the methine type may be synthesized by combining equivalent molar amounts of a chiral aniline and an aromatic aldehyde (which may also have a chiral substituent) condensing in acetic acid, and heating.

Helichromic compounds of the azo-methine type may be synthesized by several methods known to those skilled in the art. Usually such methods involve synthesis of (+)-4-(2-methylbutyl)benzaldehyde followed by condensation with various amino azo dye intermediates to produce a chiral azo-methine dye. An example of this method is illustrated below.

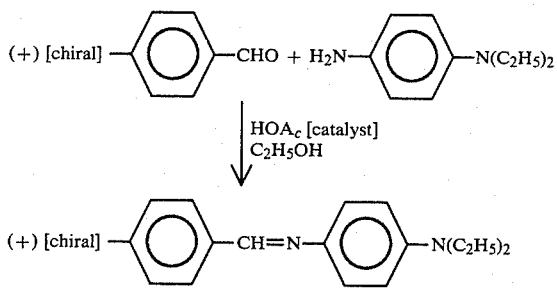

Helichromic compounds of the merocyanine type may be prepared by known methods of reacting a merocyanine dye precursor with a chiral halide. Exemplary merocyanine dye precursors are described in The Chemistry of Synthetic Dyes, Monograph No. 127, pages 249–254 (1955).

Helichromic compounds of the methine-arylidene type are synthesized as shown in U.S. Pat. No. 4,033,948, incorporated herein by reference.

Helichromic anthraquinone type compounds useful in the present invention may be synthesized by substituting an optically-active amino group onto a dichroic anthraquinone starting compound. Useful dichroic anthraquinones are disclosed in applicant's copending patent application U.S. Ser. No. 70,421, in U.S. Pat. No. 3,960,750, and in U.S. Pat. No. 3,960,751. It is known that anthraquinones substituted with certain arylamino, heterothio, arylthio, or aminoalkyl groups are dichroic.

Helichromic anthraquinone dicarboximide type compounds may be synthesized by cyclizing the anthraquinone dicarboxylic acid or anhydride with a chiral amine at high temperatures, i.e., greater than 150° C., and high pressures, i.e., greater than about 10 atmospheres.

An example of a synthesis of a helichromic anthraquinone-type compound of the invention is the following:

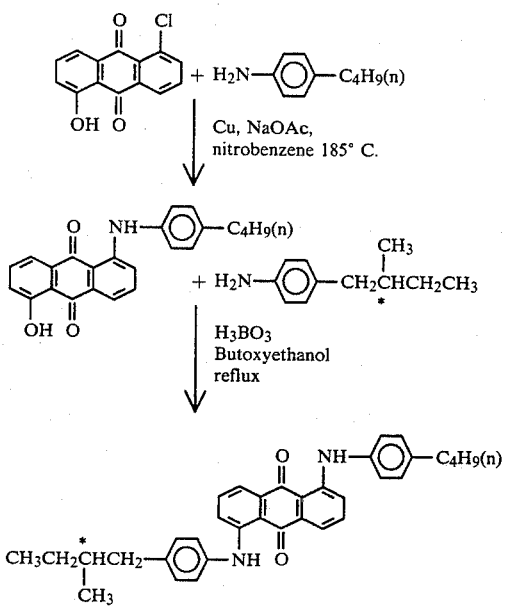

Helichromic compounds of the tetrazine type are synthesized by dehydration of the appropriately-substituted benzaldoxime using hydrazine, followed by oxidation to the appropriate tetrazine.

Helichromic compounds of the oxadiazine-type may be synthesized by first preparing the appropriately substituted triphenodioxazine by condensation of chloranil and the appropriately substituted arylamine in alcohol and in the presence of an acid binder such as magnesium oxide. This is followed by oxidative ring closure which is accomplished by refluxing the appropriately substituted triphenodioxazine in a high boiling solvent, such as nitrobenzene, and in the presence of a catalyst such as phosphorus pentachloride.

Helichromic compounds of the carbazole-azo-type may be synthesized by the condensation of a tetra-azotized diaminocarbazole with two equivalents of the appropriately substituted benzene in water buffered with sodium acetate.

The helichromic compounds of the invention have absorption maxima between 400 and 750 nanometers. Additionally, the helichromic compounds of the invention have, in general, relatively high values of the optical order parameter S. This parameter is a measure of the efficiency with which the compound is oriented by the liquid crystal material and is directly related to the contrast one observes when viewing the device. In general, dyes having high optical order parameters produce displays having high contrasts. The determination of the optical order parameter, S, is discussed in the Journal of Applied Physics, Vol. 45, No. 11, 4718–23 (1974).

$S=(A_o-A_1)/(A_o+2A_1)$ wherein $A_o$ is the absorbance in the absence of of an electrical field and $A_1$ is the absorbance in the presence of an electric field. S is a value something less than 1, but preferably is very close to 1. Values of S greater than 0.5 and preferably greater than 0.65 insure contrasts of between 5:1 and 10:1. The S values for the helichromic compounds of the present invention are generally greater than 0.5, and for many of the azo type helichromic compounds is greater than 0.65.

The helichromic compounds of the invention are generally more stable than the optically-active cholesteric liquid crystals disclosed in U.S. Ser. No. 251,247 as being useful in thermally-addressed cholesteric-smectic liquid crystal devices. The helichromic compounds are chemically-photochemically stable in liquid crystal display systems, i.e., moisture and ultraviolet light will not readily destroy the molecule.

In addition, since the helichromic dyes of the present invention are not themselves liquid crystalline, they do not substantially alter the thermodynamic properties of the liquid crystal mixture to which they are added, as do traditional optically-active liquid crystalline additives.

The helichromic compounds of the invention can be combined with, and are soluble in, smectic liquid crystal compositions of the A or C type. Such smectic A and smectic C type liquid crystal materials are well-known in the art and are generally substituted cyano diphenyls or esters of substituted cyano diphenyls. Preferably the smectic liquid crystals employed in the compositions of this invention have a melting point below 0° C., have a smectic to nematic transition temperature of greater than about 30° C., have a nematic to isotropic transition temperature of less than 10° C. above the smectic to nematic transition temperature, have a positive dielectric anisotropy of greater than 5, more preferably greater than 10, or a negative dielectric anisotropy of less than −5, more preferably less than −10, and exhibit a high degree of cooperative ordering of the helichromic compound.

Exemplary of the preferred smectic liquid crystal materials are the following:

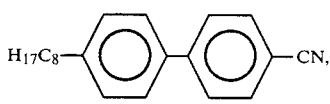

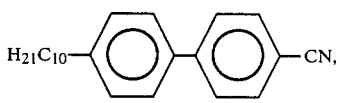

-continued

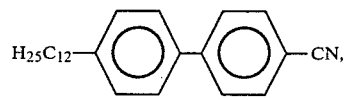

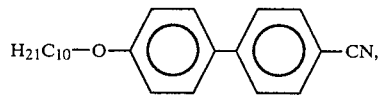

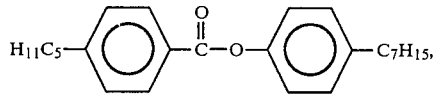

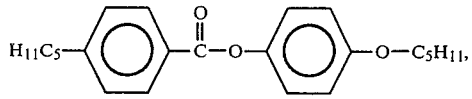

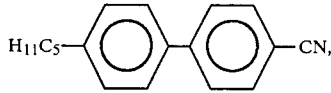

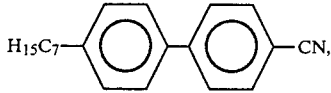

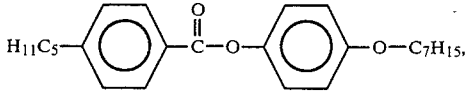

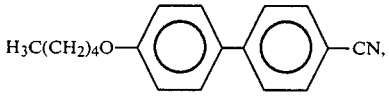

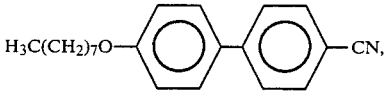

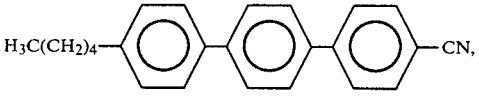

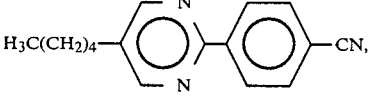

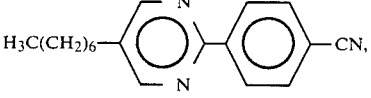

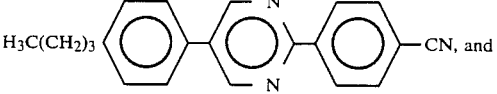

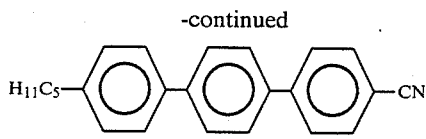

One particularly preferred smectic liquid crystal composition comprises:

$H_{17}C_8$—⬡—⬡—CN  about 26 percent by weight, $H_{21}C_{10}$—⬡—⬡—CN  about 15 percent by weight, $H_{25}C_{12}$—⬡—⬡—CN  about 32 percent by weight, $H_{21}C_{10}$—O—⬡—⬡—CN  about 16 percent by weight, and about 11 percent by weight of a eutectic mixture of biphenylpyrimidine liquid crystals commercially available as "ROTN 404" from Hoffman LaRoche. This composition has a melting point below about −5° C., a smectic nematic transition temperature of about 51.2° to 52.5° C., a nematic to isotropic transition temperature of about 54.4°–56.0° C., and an estimated dielectric anisotropy of about +18.

Another particularly preferred smectic liquid crystal composition comprises $H_{11}C_5$—⬡—C(=O)—O—⬡—O—$C_7H_{15}$  about 39 percent by weight $H_{11}C_5$—⬡—C(=O)—O—⬡—O—$C_5H_{11}$  about 28 percent by weight, and $H_{21}C_{10}$—⬡—⬡—CN  about 33 percent by weight.

This composition has a melting point of less than about 0° C., a smectic to nematic transition temperature of about 54° C., a nematic to isotropic transition temperature of about 56° C., and an estimated dielectric anisotropy of about +18.

The helichromic compound must be present in the smectic liquid crystal material in a quantity sufficient to assure that incident visible light is propagated in a circularly polarized manner, so that all polarizations of the light are absorbed. The amount of helichromic compound required to insure the absorbance of all polarizations of the incident light is dependent upon the size of the helichromic molecule and the number of optically-active groups included in the molecule. A longer helichromic molecule will result in absorption of all polarizations of light at a lower concentration than will a relatively shorter helichromic molecule. In addition, a helichromic molecule containing two optically-active groups will effect absorption of all polarizations of incident light at a lower concentration than an analogous helichromic molecule containing only one optically-active group.

Typically, the quantity of helichromic compound which will assure absorption of all polarizations of incident light is between about 0.1 and 5 percent, and preferably between about 1 and 4 percent by weight of the bulk smectic liquid crystal material.

The liquid crystal display devices of the invention comprise a smectic liquid crystal medium in admixture with at least one helichromic compound. The medium is thermally sensitive and exhibits a transition between at least two thermal phases. The upper thermal phase is a nematic phase and the lower thermal phase is a smectic phase. The mixture can develop two textures in the smectic phase: a light absorbing texture and a homeotropic transmissive texture. The homeotropic texture is developed in portions of the medium by electrically addressing the medium as it passes rapidly from the upper thermal phase to the lower thermal smectic phase. The light absorbing texture develops in the unaddressed portions of the medium as it goes through the transition to the smectic phase.

To operate the displays of the invention, the liquid crystal material is passed rapidly through its thermal transition from its lower thermal phase to its upper thermal, nematic phase. The transition must be accomplished reasonably rapidly, hence rapid thermal pulses are used that heat the liquid crystal locally but do not significantly heat the surrounding glass. The natural cooling period immediately following the passage of the heat pulse must also be such that the liquid crystal medium passes through the nematic phase to the smectic phase rapidly. This produces the optical effect, and results in images having high contrast.

While the medium is cooling, certain portions of the mixture are electrically addressed by the application of a voltage. These addressed portions develop a substantially transmissive light state and define the background of the display. The remaining unaddressed portions of the mixture develop a substantially light absorbing state as the medium passes into the smectic phase. When light is passed through the medium, the unaddressed portions appear as a dark image upon a bright background. The addressed portions of the medium may be addressed in a chronological sequence, as will be described in more detail hereinbelow. Thus, by controlling the electric field across the liquid crystal layer during the nematic to smectic phase transition, one can create at will, either a light absorbing or light transmissive state. Once these states are formed, they are stable until erased by heating into the isotropic or nematic phase again.

Although the above description states that the medium is heated into the nematic state, it is understood that it could be further heated to the isotropic state. However, only heating to the nematic state is needed. Also, due to the physical mechanisms of forming the colored scattering state, the temperature range of the nematic state should be sufficiently narrow to ensure a good display performance, i.e., less than 10° C.

There are two forms of thermally addressed smectic A and C displays. One type uses a scanning laser beam to address the display elements. This method is well-known in the art and is described in U.S. Pat. No. 4,196,974. However, a less complex form of address is achieved by the use of an x y matrix of electrodes. The row electrodes are heated sequentially with electric current pulses and the display is addressed by applying voltages to the columns. During the addressing process, only the pixels associated with the row where the heating current has just been removed are affected. In other words, only the pixels where the liquid crystal material is rapidly cooling to the smectic state respond to the writing pulses on the column electrodes. The use of thermal pulses in the row, and electric field induced switching in the column eliminates "cross-talk," soft rise, and decay of the liquid crystal material, and requires no active matrix of thin film transistor or other non-linear switches to allow discrete pixel for pixel addressing. Using this technique very high writing rates, comparable to video, are attained.

As the liquid crystal material cools rapidly through its electronically responsive mesophase to the smectic phase, the mixture of liquid crystal material and helichromic compound can form two different textures. With a voltage applied on the column, the mixture assumes a homeotropic state and on cooling assumes the transmissive homeotropic smectic A or C alignment. Without the applied voltage, a light absorbing texture is developed. This absorbing texture is the result of two unique interactions of the helichromic compound and liquid crystal material. Firstly, the helichromic compound induces the formation of extremely fine scattering domains in the liquid crystal material. Secondly, being dichroic, the helichromic compound absorbs light in a highly efficient manner. Thus, the pixels associated with a cooling row electrode can be written into a transmissive state or a light absorbing state by applying or not applying voltages on the columns.

Helichromic devices of the present invention comprise two substrates of nominal thickness spaced from a few micrometers to a few tens of micrometers apart in a parallel configuration. A confining gasket material is placed between the two substrates around the periphery in order to form an air tight, substantially water impermeable bond between the two substrates. The bottom substrate has either a smooth or a micro-lenticular inner surface upon which is applied a thermal barrier layer, row heating electrodes, and a passivation layer. The top substrate has a smooth surface upon which is applied a transparent conductive column electrode and a passivation layer. The surfaces of each inwardly facing passivated electrode pattern may be treated using techniques known in the art to insure that the helichromic-liquid crystal mixture is homeotropically oriented.

Now referring to the drawings an exploded view of a typical multiplexed, visual display device 10, is illustrated in FIG. 1. The device comprises a mixture 11, of smectic A or C liquid crystal medium in admixture with the helichromic compound. This mixture 11 is disposed between two substrates 12 and 13, respectively. The bottom substrate 13 supports a thermal barrier layer 14 upon which a plurality of row heating electrodes $r_1$, $r_2$, $r_3$, etc. are disposed. The row heating electrodes make up one half of the x y matrix for addressing the liquid crystal material 11. The row heating electrodes are made of electrically conductive, light reflective material such as silver or aluminum, which can be deposited on the thermal barrier layer 14.

The top substrate 12 supports a plurality of transparent column electrodes $c_1$, $c_2$, $c_3$, etc., which make up the remaining half of the x y matrix. The column electrodes are electrically conductive and can be formed from material such as indium tin oxide.

The liquid crystal medium 11 is generally sealed between the two substrates 12 and 13 with the electrodes in contact on either side. Light (generally ambient) is passed through (arrow 15) the composite, as shown.

Figure 2:
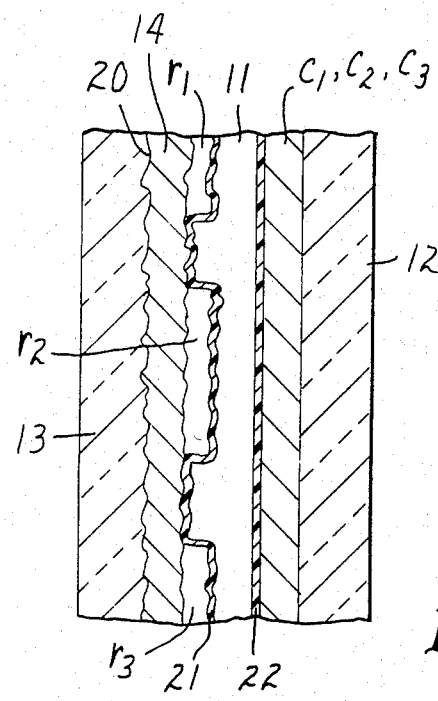
FIG. 2 is a schematic cross-sectional view of the device shown in FIG. 1.

The bottom substrate 13 is usually made of glass, but can be made of other substances such as ceramic or polymeric materials. Referring specifically to FIG. 2, the bottom substrate 13 has a micro-lenticular surface 20 which faces the interior of the cell 10. Such a microlenticular surface provides high brightness over a wide viewing angle and is described in copending U.S. Ser. No. 308,991. While, where a wide viewing angle is desired the surface of the bottom substrate 13 is microlenticular, it is understood that where a narrow viewing angle is desired the bottom substrate has a specular surface.

The micro-lenticular surface 20 consists of concave shaped cavities or dimples having a depth ranging from about 0.5 to 2.5 micrometers, and a diameter from about 10 to 20 micrometers. This micro-lenticular surface can be obtained by a combination of polishing and etching the bottom substrate. It is particularly preferred to polish a soda-lime glass bottom substrate 13 using, for example, a Highland Park Vi-Bro-Lap-model 20VL lapping machine. In order to get effective polishing action, a thin layer of a polishing mixture, such as a mixture of 30 percent by weight of 12.5 $\mu$m $Al_2O_3$ and 70 percent by weight of de-ionized water, to which 5 grams of detergent is added, is applied on the surface of the machine by brushing. The glass substrate is then polished until a uniformly diffused surface is observed. For example, the soda-lime glass can be polished for about 10 minutes to achieve such a surface. After lapping, the glass is removed from the lapping machine and thoroughly cleaned. The polished glass has a very random rough surface. This surface roughness is reduced preferably by etching the glass in an appropriate etching solution, such as 6:1 Buffered Oxide etch solution sold under the name of Buffor Oxide solution by Ashland Chemical Company, Specialty Chemical Division, Easton, Pa. Using the aforementioned Buffor Oxide solution, generally it is preferable to etch the soda-lime glass for approximately 30 minutes to achieve the desired microlenticular surface properties. After etching the surface is cleaned with an appropriate solvent or solvents, such as de-ionized water, followed by rinsing with methanol.

A thermal barrier layer 14 is deposited over the micro-lenticular surface. The thermal barrier layer 14 insulates the row electrodes $r_1$, $r_2$, $r_3$, etc., and the liquid crystal medium 11 from the bottom substrate 13, such that much of the heat generated by the row electrodes passes into the liquid crystal medium 11 and a smaller amount of the heat energy passes into substrate 13. This provides for a more efficient and efficacious use of energy; the row electrodes now requiring less electrical current in order to cause a phase change in the liquid crystal medium 11.

The insulative character of the thermal barrier layer 14 is such that it has a coefficient of heat conductivity of less than about $15 \times 10^{-4}$ cal $sec^{-1}$ $cm^{-1}$ $°C.^{-1}$. Suitable thermal barrier materials include both organic polymer layers and appropriate glass fritted layers containing air or vacuum pockets.

To be effective and practical, the barrier layer should have the following characteristics:
1. Good adherence to glass.
2. Good adherence to metal conductor layers.
3. Chemically compatible with liquid crystal materials and helichromic compounds.

4. Stable when display seal heat is applied (approximately 150° C.) for short periods of time (5-10 minutes).
5. Not subject to crazing or stress breaking over time.
6. Not subject to swell or loss of texture in the presence of liquid crystal materials over time.
7. Can be processed through conventional metal/passivation photolithography without loss of properties, and is capable of allowing line definition in the patterned layers.
8. Low thermal conductivity (less than about $15 \times 10^{-4}$ cal sec$^{-1}$ cm$^{-1}$ °C.$^{-1}$).
9. Low cost.
10. Easy to apply reproducibly.

A preferred thermal barrier material is polymonochloro-para-xylylene, commercially available as "Paralene C" from the Union Carbide Corporation. Additionally useful thermal barrier materials are thermoset or thermoplastic polymers of the imide or amide type. Alternatively, it is possible to use fritted glass composed of at least 30 percent hollow microballoons as a thermal barrier layer. The air or vacuum pockets provided by the hollow microballoons provide a good thermal insulator.

The thermal barrier layer 14 can be applied in solid form by means of knife blade, spinning, vapor or spray coating over the underlying surface. The thermal barrier layer 14 should have an approximate thickness of 0.5 to 100 microns. Where the thermal barrier layer 14 is polymonochloro-para-xylylene, it is applied by polymerizing it from its vapor state in a vacuum system, directly upon the bottom substrate 13. This method has the advantage that it allows a uniformly thick coating to be applied. Additionally, this method allows replication of the underlying micro-lenticular surface of the bottom substrate 13, thus preserving the optical properties of substrate 13. The thermal barrier layer 14 can be made with a minimum thickness of about 15 micrometers, and a preferred thickness of about 30 micrometers.

The row heating electrodes, $r_1$, $r_2$, etc., are next applied over the thermal barrier layer 14. These electrodes are made of an electrically conductive, light reflective material such as silver, gold, copper or aluminum in a thickness range of 0.1 to 15 micrometers, with a preferred thickness about 1.5 micrometers. These electrodes may be applied so as to replicate the microlenticular surface of the underlying thermal barrier layer 14, to provide high brightness and a wide viewing angle. Additionally, these electrodes may be colored, to provide a colored background for the display while it is being operated.

Top substrate 12, of transparent glass or polymeric material, is coated with column electrodes, $c_1$, $c_2$, $c_3$, etc., made from a transparent electrically-conductive material, such as indium tin oxide, and is spaced from the lower assemblage by inert polymer or glass spacers, not shown. An inert coating of a material having an index of refraction equal to or less than about 1.6 is in optical contact with the inner surfaces of the row and column electrodes and intervening areas. These layers 21 and 22 serve two purposes. The low index of refraction increases the brightness of the display by reducing total internal reflection. The material also serves as a passivation layer to protect the electrodes from oxidation and the liquid crystal material between the electrodes from contamination. Materials such as $SiO_2$, $MgF_2$ and various fluoropolymers can be used as the low index of refraction layers 21 and 22. Layers 21 and 22 are about 0.005 to 0.2 micrometers thick, and are preferably about 0.01 to 0.1 micrometers thick. Layers 21 and 22 can also serve as surface alignment layers if properly deposited. Alternatively, layers 21 and 22 have surface alignment layers, such as silane or lecithin applied over them.

Figure 3:
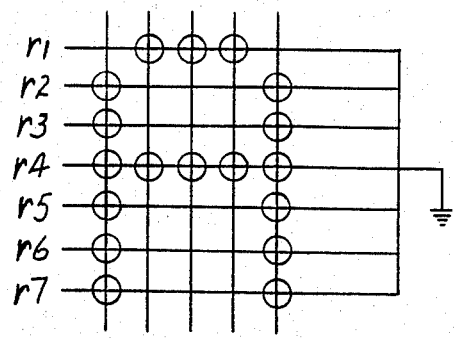
FIG. 3 is a plan schematic view of the device shown in FIG. 1, illustrating how an image can be formed in the liquid crystal medium by a multiplexing technique.
Figure 4:
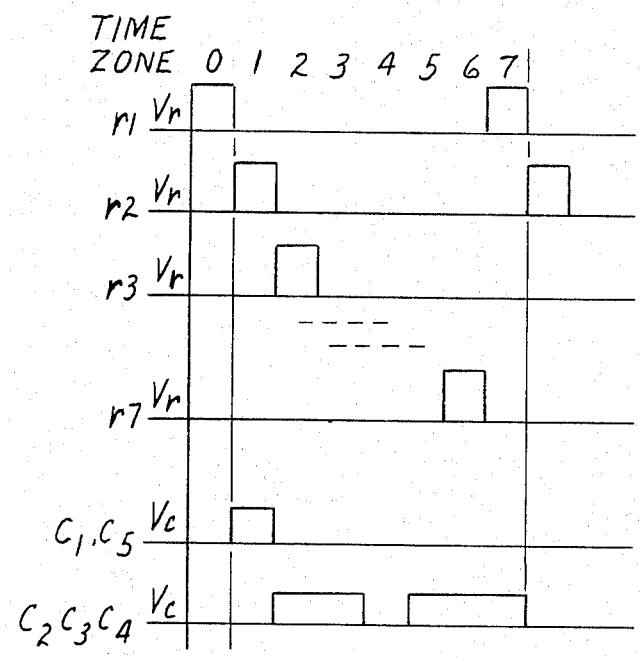
FIG. 4 is a graphical illustration of the chronological sequencing of the row and column electrical waveforms of the device depicted in FIG. 1.

The physical operation of the display 10 can best be illustrated with a simple example of a 5×7 matrix displaying a character "A," as shown in FIG. 3. The rows of the matrix are tied together at one end to the common 16 and are sequentially heated by applying electric pulses to the other ends 17. In time zone 0, (see FIG. 4) row 1 is heated such that the liquid crystal material over the row 1 electrode $r_1$ is in either the isotropic or electronically addressable nematic state. In time zone 1, row 2 electrode $r_2$ is heated. In the meantime, as row 1 cools down, the pixels associated with it are addressed by applying electric voltage on the column electrodes. In this example, electrodes $c_1$ and $c_5$ have voltage applied such that the pixels $r_1c_1$ and $r_1c_5$ will be in the clear state. $C_2$, $c_3$, $c_4$ have no voltage applied, and the pixels $r_1c_2$, $r_1c_3$, $r_1c_4$ have a colored light absorbing texture. During the time zone 2, row 3, electrode $r_3$, is heated and row 2 cools down, and the voltage on the columns assume the values corresponding to the "voltage on" and "voltage off" pattern of pixels associated with row 2. The entire waveform for displaying a character "A," is shown in FIG. 4.

The colored light absorbing texture associated with the voltage off state pixels is metastable and has long relaxation time generally up to several months. The erase-writing process for this display is very fast. Generally, less than a 100 micro-second writing time can be achieved. If the display is refreshed at $f_r$ times per second, the total number of rows that can be multiplexed will be:

$$n = 1/(f_r \times T_W)$$

When $T_W$=the time required to write the row.
With $f_r$=30 hertz, which is the rate similar to a conventional CRT, and
$T_W$=100 microsec.
n=333 rows.

Thus, the display can be multiplexed up to a rather large number of rows. In practical display driving, the heating pulse can be applied over several time zones before the cooling and writing cycle. The heating pulse should be short enough to avoid heat spreading to the neighboring rows. A high contrast ratio, on the order of about 10 or 20 to 1, is achieved for the colored or black image due to the light absorbing character of the helichromic compound vis-a-vis the transparent background. The thermal barrier layer allows contrast saturation at a lower overall thermal energy density than is required for displays which do not utilize such a thermal barrier layer.

The contrast ratio is further improved by the reflective nature of the row electrodes which replicate the micro-lenticular surface of the bottom support plate 13.

The helichromic-smectic devices of this invention have several advantages over the smectic liquid crystal devices of the prior art. The helichromic devices require no auxiliary polarizers. Additionally, when compared with the smectic-cholesteric liquid crystal displays disclosed in U.S. Ser. No. 251,247 (which also do not require auxiliary polarizers) the helichromic displays are more efficient since they can be operated at lower voltages, with faster response times and greater contrasts.

The voltage required to operate a helichromic device having equivalent brightness is less than about one-quarter that required to operate a corresponding smectic-cholesteric device. Voltages of about 4 to 6 volts are required to operate high brightness helichromic displays while voltages of about 25 to 28 volts are required to operate corresponding smectic-cholesteric devices offering similarly high brightness. Additionally the image contrast offered by helichromic displays is at least twice as high as corresponding smectic-cholesteric devices of similar brightness. Typical helichromic display contrast ratios are between about 10 and 16, while corresponding smectic-cholesteric display contrast ratios are between about 5 and 7.

Furthermore, the response times of helichromic displays are much faster than the response times of corresponding smectic-cholesteric displays. Response times for helichromic displays are about 10 to 20 microseconds, while response times for similar smectic-cholesteric displays are about 30 to 70 microseconds.

Another significant advantage of devices utilizing the helichromic compounds of the present invention is that the smectic liquid crystal material need be adulterated with relatively less foreign additive, i.e. helichromic compound than do corresponding smectic-cholesteric devices, thereby reducing potential sources of device decomposition. In general, substantially more dichroic dye and optically-active dopant must be present in smectic-cholesteric displays to attain equivalent brightness as compared to displays containing only between 0.1 and 5% by weight helichromic compound.

It is believed that the helichromic compounds of the invention provide helichromic displays which can be operated more efficiently than smectic-cholesteric displays, because the helichromic compounds do not absorb incident light by physically cholesterically ordering mixtures of smectic liquid crystals, but instead absorb incident light by propagating the light in a circularly polarized manner so that all polarizations of the incident light are absorbed. Since the helichromic devices are not required to change from a homeotropic to a cholesteric ordering in order to operate, they can be operated at lower voltages, with shorter response times than can smectic-cholesteric displays which must alternate between homeotropic and cholesteric alignment.

The following examples illustrate helichromic compositions and devices in accordance with the invention. It should be understood that this is done solely by way of example and is intended neither to delineate the scope of the invention nor limit the ambit of the claims. Examples 1–12 describe intermediates useful in the preparation of the helichromic dyes, described in Examples 13–31. Examples 32–35 illustrate the use of helichromic compounds in thermally addressed liquid crystal displays. In the examples which follow and throughout the specification, the quantities of material are expressed in terms of percentages by weight of the total composition, unless otherwise specified.

EXAMPLE 1

The intermediate (+)-2-methylbutyl bromide was prepared by mixing (+)-2-methyl-1-butanol (300 gm 3.4 moles), with 100 ml. of pyridine. Over a period of 5 hours 513 gm (3.40 mole) of PBr₃ was added to the mixture. The temperature of the reaction mixture during the PBr₃ additions was maintained at 20°-25° C.

The product was then distilled under reduced pressure to give 485 gm of crude (+)-2-methylbutyl bromide. The crude material was dissolved in 1 l. of petroleum ether (b.p. 30°-60° C.) and was washed in succession with first 5% NaOH, then water, then 10% H₂SO₄, then concentrated H₂SO₄ and finally water again. After drying over anhydrous calcium sulfate the petroleum ether was stripped off and the product was fractionated at atmospheric pressure. (+)-2-methylbutyl bromide (397 gm) was recovered (b.p. 119°-121° C.). Nuclear Magnetic Resonance (NMR) and Infrared (IR) spectra confirmed the proposed structure of the product $[\alpha]_D^{20} = 3.9°$

EXAMPLE 2

The intermediate (+)-2-methylbutyl benzene was prepared by the procedure described hereinbelow.

(a) Preparation of the catalyst [dichloro-1,2-bis( diphenyl-phosphino)ethane]nickel (II).

A solution of 1,2-bis(diphenylphosphino)ethane (4 gm), prepared according to the method of Tamao et al., J.A.C.S., 94, 4735 (1974), dissolved in 400 ml warm ethyl alcohol was added to 2.4 gm hydrated nickel chloride in 20 ml ethyl alcohol. The product crystallized as dull orange needles.

(b) Preparation of (+)-2-methylbutyl magnesium bromide.

Magnesium turnings (38.3 gm) were placed in a dry 2 liter flask equipped with dropping funnel, nitrogen inlet, and stir bar. Dry nitrogen was led in and the magnesium turnings were subjected to stirring overnight.

(+)-2-methylbutyl bromide (5 gm), prepared according to the procedure of Example 1, in 125 ml dry ether was run into the flask followed by 221.7 gm (+)-2-methylbutyl bromide in 1 liter of ether which was dropped in at a rate sufficient to maintain the reaction. The Grignard reagent was refluxed for one hour after addition was completed.

(c) Preparation of (+)-2-methylbutyl benzene.

To a mixture of the nickel catalyst prepared in step (a) (208 gm, 0.39 mmol), chlorobenzene (135 mmol) and ether (50 ml) was added (+)-2-methylbutyl magnesium bromide (60 mmol), prepared in step (b), in 50 ml ether. The mixture was kept at 0° C., with stirring, over 10 minutes. The resulting mixture was heated to reflux for 20 hr. The reactants were cooled to 20° C. and 10% hydrochloric acid was added to hydrolyze the mixture. Sodium chloride is added to saturate the aqueous layer and the water phase was extracted with 3-50 ml portions of ether. The combined extracts are washed with water, dried over calcium chloride, and concentrated in vacuo. The residue was distilled under reduced pressure and the product, which boiled at 91° C. (25 mm Hg), was collected. The structure of the product was confirmed by NMR.

EXAMPLE 3

Preparation of the intermediate (+)-4-(2-methylbutyl)-nitrobenzene

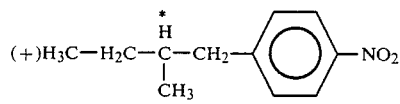

(+)-2-Methylbutylbenzene, prepared according to the procedure of Example 2, (0.75 mol, 111.0 gm) was added to 200 ml glacial acetic acid. This solution was added dropwise to a mixture of 420 ml 90% fuming nitric acid and 180 ml glacial acetic acid, which had been cooled at −20° C. Maintaining that temperature, the mixture was stirred for one hour and then poured into 2.5 l of ice water. The reaction products were extracted with 2-500 ml portions of petroleum ether (30°–60° C.) and the combined extracts were successively washed with water (2-100 ml portions); 5% sodium hydroxide (2-100 ml portions), 10% sodium hydroxide (2-100 ml portions); and water (3-100 ml portions). The extract was dried over anhydrous calcium sulfate, the solvent was removed under reduced pressure and the resultant light yellow oil fractionated under reduced pressure. The fraction boiling at 158°–160° C. (14 mm Hg) was collected, giving a 38% yield of the product. The structure was confirmed by NMR.

EXAMPLE 4

Preparation of the intermediate (+)-p-(2-methylbutyl)aniline

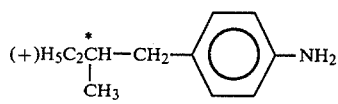

A mixture of (+)-4-(2-methylbutyl)-nitrobenzene, prepared according to the procedure of Example 3, (0.152 mol, 29.4 gm), 90 ml anhydrous ethyl alcohol, 3.05 gm activated carbon and 0.032 gm ferric chloride hexahydrate was refluxed for 10 minutes. Hydrazine hydrate (12.16 gm) was then added through a dropping funnel over a period of 15 minutes. Reflux was continued for 5 hours and the mixture was filtered while still hot. The solvent was removed under reduced pressure leaving 24.5 gm of amber liquid. This was then added to a mixture of 75 ml HCl and 150 ml water. The mixture was extracted using 200 ml ether. The aqueous phase was rendered strongly alkaline using sodium hydroxide pellets and the oily product was extracted with ether. The ether extracts were dried over sodium hydroxide pellets and the ether was evaporated. The resultant amine residue was then distilled and a 77% yield of (+)-p-(2-methylbutyl-aniline having a boiling point of 89°–90° C. (1 mm Hg) was recovered. Confirmational analysis (NMR and IR) verified the product. $[\alpha]_D^{20} = 11.8°$.

EXAMPLE 5

Preparation of the intermediate (+)4-(2-methylbutyl)-benzaldehyde

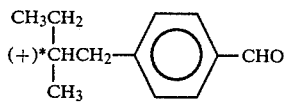

Trifluoroacetic acid (150 cc) was added to a flask containing 14.0 gm hexamethylenetetramine (HMTA). (+)2-methylbutylbenzene (14.8 gm) was then added and the mixture was refluxed for 21 hours. The deep orange mixture was distilled to remove excess trifluoroacetic acid. When about one third the volume remained, the mixture was poured into 600 ml ice water and stirred for 15 minutes. Sodium carbonate was added with stirring until the mixture was basic and the product was extracted with ether. The ether extract was washed with water and dried over sodium sulfate. The ether was removed leaving 18 gm crude (+)-4(-2-methylbutyl)benzaldehyde. This was vacuum distilled (78° C. at 0.07 mm Hg). The structure of the product was confirmed by NMR. The yield of the product was 78%.

EXAMPLE 6

The intermediate (+)-N-2-methylbutyl-α-naphthylamine was prepared by the procedure described below.

(a) Preparation of the secondary triflamide of α-amino naphthalene.

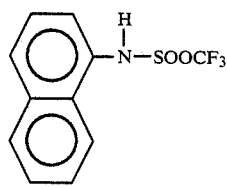

According to the method disclosed by Hendrickson et al. in "Tetra.lett," 39,3839 (1973), 1 mole of α-naphthylamine (1429 g) was dissolved in 750 ml dichloromethane and cooled to 0° C. Trifluoromethanesulfonic anhydride was then added dropwise, not allowing the temperature of the reaction mixture to rise above 15° C. at any time during the addition. When the addition was complete, the reaction mixture was allowed to warm to 20° C. and was then poured into 4 liters of ice water with rapid agitation. The organic phase was allowed to separate from the water phase and as much of the water layer as was possible was decanted. The remaining organic layer was extracted with three 500 ml portions diethylether. The drying agent was removed from the diethylether extracts by filtration and the diethylether was removed using a rotary evaporator. A 78% yield of trifluoromethanesulfonamido-α-naphthalene (300 gm) was recovered.

The above product was dissolved in 3 liters boiling carbon tetrachloride and 200 gm activated carbon was added. The mixture was immediately filtered while hot, and colorless platelets of pure triflamide of α-aminonaphthalene were recovered by filtration. The product was dried in an oven overnight. Pure triflamide of α-aminonaphthalene having a melting point of 112.9° C. was recovered in an 80% yield. The structure of the product was confirmed by IR, NMR and mass spectroscopy.

(b) Preparation of the sodium salt of trifluoromethanesulfonamido naphthalene.

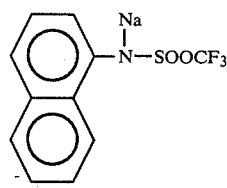

Sodium metal (4.91 gm) was dissolved in 200 ml absolute anhydrous ethanol and 58.7 gm of the triflamide of α-amino naphthalene prepared in step (a) was added. The compound dissolved immediately and the mixture was refluxed, for 30 minutes. The flask containing the reaction mixture was then fitted with a Dean-Stark water collector and an addition funnel. The volume of solvent ethanol was reduced by approximately 50% and the reflux temperature was recorded at 74° C. 200 ml benzene was added and the reflux temperature dropped to 64° C. The azeotrope was selectively removed from the trap and when the remaining volume in the flask was about 100 ml, 200 more mls of benzene was added. The salt began to crystallize in the reflux when the reflux temperature was about 80° C. indicating removal of ethanol and water. The flask was removed from the trap and the remaining benzene was removed by a rotary evaporator yielding 63 gm of the sodium salt of trifluormethanesulfonamido naphthalene in a 99.2% yield. The structure of the product was confirmed by an IR spectra.

(c) Preparation of (+)-N-(2-methylbutyl)-N-trifluoromethylsulfonyl-α-naphthylamine

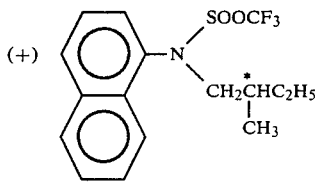

62.91 gm of the product obtained in step (b), 45 gm potassium iodide and 45 gm (+)-2-methylbutylbromide, prepared according to the procedure of Example 1, were dissolved into 500 ml dimethylformamide and refluxed 66 hours. The reaction mixture, containing precipitated KBr, was drowned in 1 liter water and extracted with 500 ml chloroform. The chloroform solution was dried using magnesium sulfate and the chloroform was removed using the rotary evaporator. The oily product remaining is vacuum distilled at 1 mm of mercury. The product collected at 150°-180° C. was the desired product (+)-N-(2-methylbutyl)-N-trifluoromethylsulfonyl-α-naphthylamine.

(d) Hydrolysis of (+)-N-(2-methylbutyl)-N-trifluoromethylsulfonyl-α-naphthylamine to yield (+)-N(2-methylbutyl)α-naphthylamine.

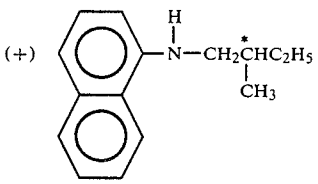

The drying agent calcium hydride (10 gm) was allowed to stand overnight in 1 liter of diglyme. The dried diglyme was decanted into a flamed out distilling flask and lithium aluminum hydride was added in small portions until no further effervesence occurred upon addition. The diglyme was then distilled at 15 mm, bp 62°-3° C., making sure only 500-600 ml were distilled into the receiving flask. This diglyme was stored over dry N$_2$.

A 500 ml round bottom flask fitted with a condenser, mechanical stirrer, and addition funnel fitted with drying tubes, was flame dried and charged with 400 ml of the dry diglyme. 180 ml 1M lithium aluminum hydride in diethylether was poured into the addition funnel and slowly added to the diglyme. A white precipitate formed which redissolved upon warming the mixture. The mixture was then heated and the diethylether removed from the diglyme. The temperature of the diglyme/lithium aluminum hydride solution was kept at 105° C.

1.5 gm of the product of step (c) was dissolved in 100 ml of the dry diglyme and placed into the addition funnel. This solution was then slowly dropped into the hydride solution and when the addition was complete the funnel was removed, the thermometer added, and the temperature raised to a constant 110° C. The reaction was allowed to proceed for 16 hours and the resultant cloudy yellow mixture was allowed to cool to 20° C.

The reaction mixture was transferred to a large 1 liter dropping funnel and slowly dropped into 1 liter of water with constant stirring. The mixture was diluted to 6 liters with water and one liter at a time was extracted with 500 ml portions of diethylether. In each extraction 100 ml of a 25% by weight NaOH in water solution was added during the extraction. The combined ether extracts were washed twice with 1 liter water and were dried with magnesium sulfate.

The ether was removed by vacuum evaporation and the remaining oil was distilled from NaOH pellets at reduced pressure. The fraction boiling over at 0.7 to 1.0 mm, 144°-153° C., was the desired product in 80% yield. The structure of the product was confirmed by IR and NMR.

EXAMPLE 7

Preparation of the intermediate (+)-N-citronellyl-naphthylamine

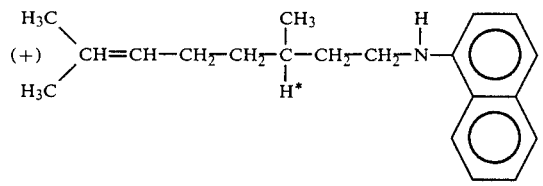

was prepared according to the procedure disclosed by Borsch et al. in J.A.C.S., 93, 2897 (1971).

2.0 g α-naphthylamine (14 mmol) and 0.01 gm α-naphthylamine-HCl were added to 25 ml absolute methanol along with 2.15 gm citronellal (14 mmol) and stirred for five minutes, after which the solution turned hazy. Then 0.53 gm (8.4 mmol) sodium cyanoborohydride was added and a brief exotherm occurred. The mixture was stirred overnight at room temperature. The bottom organic layer was separated from the top aqueous layer. An IR spectra of the organic layer (a brown oil) showed no carbonyl group and very little absorption in the OH/NH region (330-360 nm). Upon vacuum distillation of the organic layer the component having a bp of 175°-180° C. was collected. The desired product was recovered as a pale yellow oil in 21% yield. The structure of the amine product was confirmed by NMR.

EXAMPLE 8

Preparation of the intermediate
(+)-N-camphanyl-α-naphthylamine

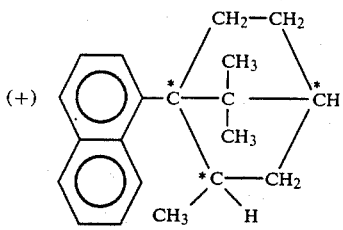

Camphor (10 gm), 9.4 gm α-naphthylamine, 0.1 gm α-naphthylamine-HCl and 30 gm 1 Å molecular sieves were added to 40 ml anhydrous methanol. Sodium cyanoborohydride (2.5 gm) was added dropwise and stirred under $N_2$ for 48 hours. The sieves were removed by filtration and 5 drops of concentrated HCl were added to the filtrate until it was acidic (pH>7). The solvent was stripped by boiling and 10 gm potassium hydroxide was added to the remaining mixture. The aqueous phase was extracted with ether over potassium carbonate. The extractions were filtered to remove the potassium carbonate. After the ether was evaporated, the mixture was distilled under high vacuum. The material boiling at 120° C. and 0.1 mm of mercury was collected. IR spectra verified that this material was the product.

EXAMPLE 9

Preparation of the intermediate
(+)-N-(3-methylcyclohexyl)-α-naphthylamine

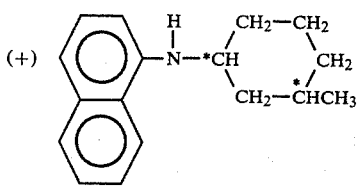

The procedure described in Example 15 was repeated except that the 10 gm of camphor was replaced by 7.4 gm of 3-methylcyclohexanone. The material boiling at 145°-160° C. and 0.1 mm of mercury was collected. IR spectra verified that this material was (+)-N-(3-methylcyclohexyl)-α-naphthylamine.

EXAMPLE 10

Preparation of the intermediate
(+)-4-methylhexylaniline

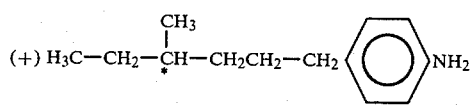

Using the procedure of Example 1, (+)-4-methylhexan-1-ol, prepared according to Example 10, is converted to the corresponding optically-active bromide. Then, according to the procedure of Example 2, the optically-active bromide is converted to (+)-4-methylhexylbenzene. Then, following the procedures described in Examples 3 and 4, the (+)-4-methylhexylbenzene is nitrated and reduced to (+)-4-methylhexyl aniline. The structure of the product is confirmed by NMR.

EXAMPLE 11

Preparation of the intermediate
(+)-p-(2-methylbutyl)phenylazo-[2,5]-dimethylphenylazo-[2,5]-dimethylaniline

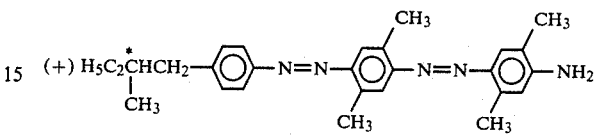

(+)-p-(2-methylbutyl)aniline (16.1 gm), prepared according to Example 4, was dissolved in 100 ml concentrated hydrochloric acid and 50 ml of water was added to disperse the acid salt. The slurry was cooled to 0° C. and diazotized by adding dropwise 6.9 gm $NaNO_2$ in 30 ml water. After the completion of diazotization, as indicated by starch-iodide paper, the clear diazonium is added to a mixture of 12.1 gm 2,5-dimethylaniline in 100 ml glacial acetic acid. Coupling occurred and a saturated sodium acetate solution was added to adjust the pH to 5.0. The bright red product was collected by filtration and redispersed in 50 ml water. A solution of 20% by weight sodium carbonate in water was added until the pH was greater than 7. The product was filtered, washed and dried to yield (+)-p-(2-methylbutyl)phenylazo-[2,5]-dimethylaniline in 85% yield.

The above product (28 gm) was dissolved in 100 ml 87% sulfuric acid in water and diazotized by the dropwise addition of nitrosylsulfuric acid at 10° C. until diazo formation was complete. To this solution was added 12 gm 2,5-dimethylaniline dissolved in 25 ml glacial acetic acid. After coupling was complete the mixture was diluted with ice water and neutralized using a 20% by weight sodium hydroxide solution. The helichromic intermediate was recovered by filtration in a 60% yield. The structure of the helichromic intermediate was confirmed by NMR.

EXAMPLE 12

Preparation of the intermediate
(+)-p-(2-methylbutyl)phenylazo-(phenylazo)aniline

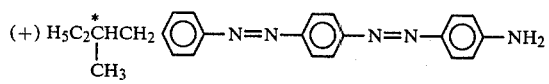

This intermediate was prepared according to the procedure of Example 11 by substituting aniline for the 2,5-dimethylaniline.

PREPARATION OF HELICHROMIC COMPOUNDS

EXAMPLE 13

Helichromic (+)-1-[4-(2-methylbutyl)phenylazo](2-hydroxy)naphthalene

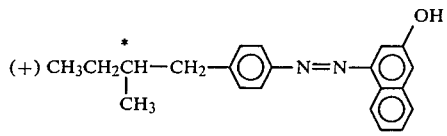

(+)-4-(2-methylbutyl)aniline prepared according to the procedure of Example 4, (0.012 mol, 2.0 gm) was dissolved in 5 ml concentrated hydrochloric acid and 5 ml water. Upon cooling to 0° C., sodium nitrite (0.015 mol, 0.85 gm) was added slowly while maintaining the temperature at 0°–5° C. When the amine was completely diazotized (a negative reading on starch-iodide paper), coupling was effected by slowly adding the cold diazonium solution to an ice cold solution of 2-naphthol (0.012 mol, 1.72 gm) dissolved in 10 ml 10% NaOH. Immediately an orange precipitate of the azo formed. After 30 minutes the precipitate was filtered, washed with water, vacuum dried and recrystallized from 50 ml of methyl alcohol. The orange colored needles melted at 74°–75° C. $\lambda_{max}^{CHCl_3}$ = 490 nm. Elemental analysis confirmed the structure of the product.

EXAMPLE 14

Helichromic (+)-1-methylamino-4-[4-(2-methylbutyl)anilino]anthraquinone

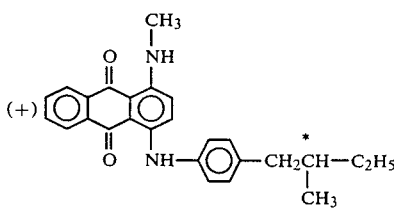

was prepared by mixing 2.0 gm (0.0063 mol) of 1-methylamino-4-bromo-anthraquinone, 2.51 gm (0.0063 mol) of (+)-4-(2-methylbutyl)aniline (prepared according to the procedure of Example 4), 2.6 gm of potassium acetate and 0.05 gm of hydrated copper acetate in 10 ml of nitrobenzene and heating under nitrogen at 160°–170° C. for a period of about 8 hours. Nearly all the nitrobenzene was then distilled off under vacuum in an oil bath heated to 125° C. After cooling to room temperature 100 ml of toluene was added to dissolve the colored product and the insoluble material was filtered off. The toluene filtrate was then chromatographed on silica gel using toluene as an eluent. Fractions containing the deep blue product were combined, stripped of solvent, and the residue was crystallized from ethanol giving 1.5 gm dark purple iridescent crystals, m.p. 95°–7° C.

$\lambda_{max}^{CHCl_3}$ of 647 and 603 nm and NMR and IR analysis confirmed that the product obtained was (+)-1-methylamino-4-[4-(2-methylbutyl)anilino]anthraquinone.

EXAMPLE 15

Helichromic 4-(N,N'-dimethylamino benzylidene)-4'-(2-methylbutyl)-aniline

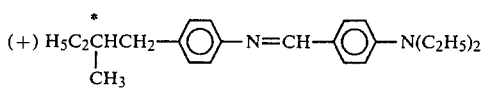

was prepared by mixing 3.26 gm (0.02 mol) (+)-4-(2-methyl-butyl)aniline (prepared according to the procedure of Example 4) 3.55 gm (0.02 mol) p-N,N'-diethyl-aminobenzaldehyde and 6 gm of "Linde" molecular sieve 3 Å (available from the Linde Corp., N.Y., N.Y.) in 20 ml of methanol and refluxing the mixture under a nitrogen blanket for 1½ hours. The sieves were then filtered off, washed with methanol and stripped of solvent on a rotary evaporator under reduced pressure, leaving a viscous yellow oil. This oil was vaccum distilled twice, b.p. 221°–3° C./0.3 mm, giving a yellow oil which solidified upon cooling. NMR and IR spectra confirmed the structure of the product.

EXAMPLE 16

(+)Bis(1,1'-(2-methylbutyl)phenylazo)[-4,4'-azonaphthyl)azophenyl]azobenzene

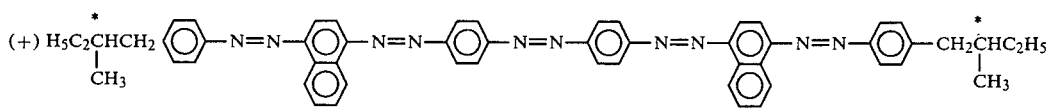

Azodianiline (0.1 mol, 2.1 gm) was tetrazotized using 2 equivalents (1.4 gm) sodium nitrite in 20 ml concentrated hydrochloric acid at 0° C. Two equivalents 1-naphthylamine were dissolved in 40 ml 1:1 glacial acetic/formic acid and cooled to 0° C. to produce a coupling solution. The clear tetrazonium solution was stirred into the coupling solution and the mixture was stirred 90 minutes at 0°–5° C. The bis-naphthyl intermediate was recovered and converted to the bis-nitroso derivative using Caros acid. Two equivalents (3.2 gm) (+)-4-(2-methylbutyl)aniline, prepared according to Example 4, were coupled by stirring the bis-nitroso derivative into the chiral aniline in glacial acetic acid at 0° C. Upon completion of coupling the solution was neutralized using sodium carbonate and the precipitated helichromic compound was recovered by vacuum filtration. The helichromic dye was purified by chromatography on silica gel using methylene chloride.

EXAMPLE 17

(+)-4-(2-methylbutyl)-4'-(5-nitrothiazolylazo)azobenzene

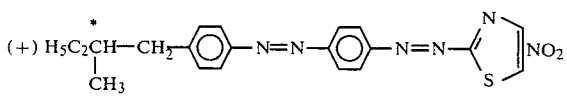

5-nitro-2-amino-thiazole was diazotized in mineral acid using sodium nitrite and coupled in the conventional manner with one equivalent aniline. Recovery of the free base of the monoazo dye and subsequent condensation of one equivalent of thin dye with one equivalent (+)-4(-2-methylbutyl)4'-nitrosobenzene in a minimum quantity of glacial acetic acid affords the helichromic dye upon recovery from the reaction mixture. Column chromatography on alumina using chloroform yields the pure dye.

EXAMPLE 18

Helichromic (+)-1,4,5-tri[4-(2-methylbutyl)phenylanilino]anthraquinone

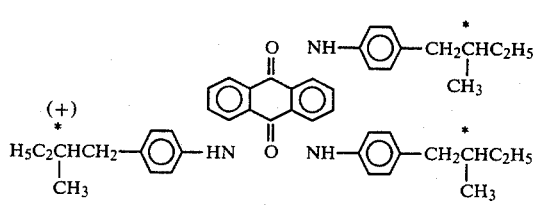

1,4,5-Trichloroanthraquinone (1.56 gm 0.005 mol) prepared by the method of A. Goldbergm J.C.S., 1791 (1931) was dissolved in 20 ml of hot nitrobenzene. Then 4.9 gm (0.03 mol) of (+)-4-(2-methylbutyl)aniline, 5.8 gm of potassium acetate and 0.1 gm of copper acetate were added. The mixture was then heated under nitrogen slowly to 200° C. and the course of the reaction was followed by thin layer chromatography (TLC) on silica gel with 1:1 toluene/hexane. When the mixture was predominantely the tri-substituted dye (TLC-cyan spot) heating was continued for another 15 minutes at 215° C. The mixture was then cooled. The reaction mixture was diluted with 250 ml of methanol and a dark blue viscous material separated. This was chromatographed twice using silica gel and 1:1 toluene/hexane as an elutant. The fractions containing the cyan dye were combined and stripped of solvent leaving a viscous residue. The viscous material was then heated under high vacuum to remove any solvent and on cooling, the dye solidified. TLC, NMR and IR analysis indicated this was the desired, essentially pure, tri-substituted dye.

EXAMPLE 19

Helichromic(+)-2-[4-(2-methylbutyl)benzylidene]-1-Ethyl-1,2-dihydroquinoline

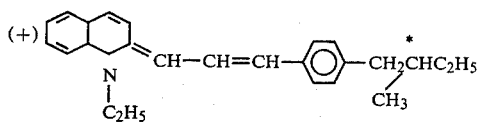

(+)-4-(2-methylbutyl)aniline can be converted to the corresponding (+)-4-(2-methylbutyl)fluorobenzene by the well-known Schiemann reaction. By refluxing a mixture of 0.1 mole of the fluorobenzene derivative and 0.1 mole of quinaldine ethyltosylate in 100 ml of acetonitrile and 0.2 mole of diisopropylethylamine for 5-6 hrs, the arylidene dye is formed. The dye can be isolated and purified by column chromatography.

EXAMPLE 20

Helichromic (+)-Bis-1,5-(α-methylbenzylamino)anthraquinone

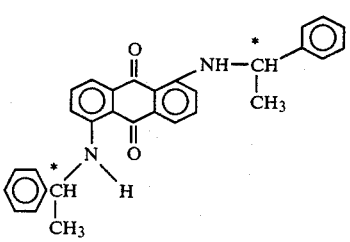

Five gm of 1,5-dichloroanthraquinone was combined with an excess (10 gm) of (+)-α-methylbenzylamine ($[\alpha]^{23} = +38°$) and heated at 150° C. for 4 hours. Column chromatography using silica gel and toluene as the eluent, and recrystallization 3 times from hexane yielded the pure desired product.

The pure product had a melting point of 134°-136° C. and its structure was confirmed by NMR.

EXAMPLE 21

Helichromic (+) 4-phenylazo-4'[4-(3-methylcyclohexylamino)]naphthylazo azobenzene

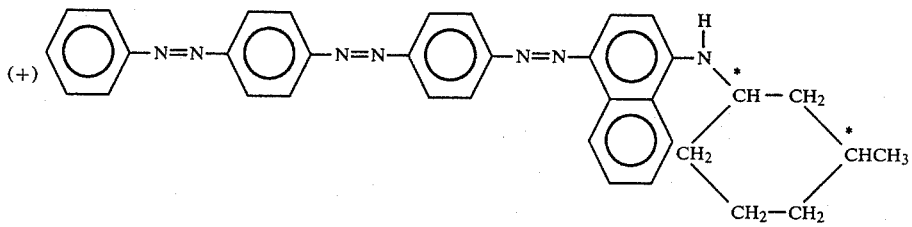

Phenylazo aniline (0.1 mol) was dissolved in 50 ml of a 20% HCl in water solution and cooled to 0° C. in an ice bath. This compound was diazotized using 0.1 mole of sodium nitrite in 20 ml of water, added dropwise. When diazotization was complete coupling was effected by stirring the product into 0.1 mole of (+)-N-(3-methylcyclohexyl)-α-naphthylamine, prepared according to the procedure of Example 9, in 50 ml of glacial acetic acid. After coupling had occurred the mixture was neutralized using a 20% by weight solution of NaOH in water, and filtered. The pure helichromic compound was recovered by chromatography on silica using 4:1 toluene/methanol as the eluent. IR and NMR confirmed the structure of the product ($\lambda_{max}$ in toluene (Tol) was 520 nm).

EXAMPLE 22

Helichromic (+)-Bis-(citronellyl)aminonaphthyl-αazo dye

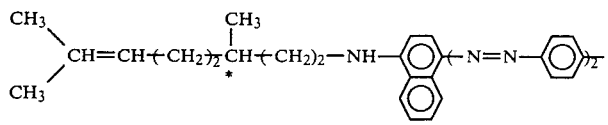
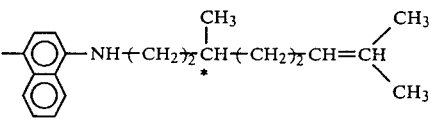

Two equivalents of the intermediate prepared in Example 7 were coupled to 1 equivalent of tetrazotized azodianiline per the procedure described in Example 16. The resulting blue helichromic dye was purified by chromatography on alumina using 4:1 toluene/methanol as the eluent. The structure of the product was confirmed by IR and NMR ($\lambda_{max}^{Tol}=595$ nm).

EXAMPLE 23

Helichromic (+)-1,4-diaminoanthraquinone-N-(2-methylbutyl)-2,3-dicarboximide

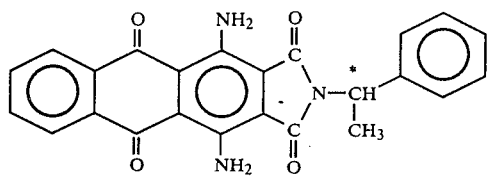

(a) Preparation of 1,4-diamino-2,3-anthraquinone-dicarbonitrile

According to the procedure disclosed in German Pat. No. 1,108,704, to 750 ml water was added in succession 18 gm sodium cyanide, 0.3 gm ammonium vanadate, 3.2 gm sodium acetate trihydrate, and 14 gm 1,4-diamino anthraquinone-2-sulfonic acid. This mixture was stirred and heated at 90° C. for 1 hour. Air was then bubbled through the mixture and after 4 hours a blue precipitate was recovered by filtration. This precipitate was water washed and oven dried to recover the desired product in quantitative yield.

(b) Preparation of 1,4-diamino-2,3-anthraquinone dicarboximide.

According to the procedure described in U.S. Pat. No. 2,753,356, to a hot (80° C.) stirred solution of 630 parts by weight 98.2% sulfuric acid in water, 126 parts by weight dried powdered 1,4-diamino-2,3-anthraquinone-dicarbonitrile, prepared according to Step (a) above, is added. An exothermic reaction occurs with the temperature rising to 140° C. The mixture is heated for 1 hour at 150° C. and is then cooled to about 40°-45° C. Keeping the mixture at this temperature, enough water (255 parts by weight) is added dropwise to make a 70% by volume acid solution. After cooling to room temperature, orange crystals are obtained and are separated by filtration. The orange crystals are washed with a 70% solution of sulfuric acid in water. The orange crystals are then slurried with water, keeping the temperature at about 70° to 80° C., for 90 minutes during which time the crystals changed from an orange to a blue color. The blue crystals are separated by filtration and are washed with hot water until the filtrate was acid free. After drying the product 1,4-diamino-anthraquinone-dicarboximide is obtained in a 73% yield.

(c) Preparation of 1,4-diaminoanthraquinone-N-(2-methylbutyl)-2,3-dicarboximide.

Also according to the procedure described in U.S. Pat. No. 2,753,356, a mixture of 40 parts by weight 1,4-diaminoanthraquinone-2,3-dicarboximide, prepared according to Step (b) above, 14 parts by weight (+)-2-methylbutylamine, 158 parts by weight methanol and 240 parts by weight nitrobenzene is heated for 16 hours at 175° C. The mixture is cooled to room temperature and the desired product is isolated by filtration. After washing with methanol and then water, the product yield is 90% of theoretical. The structure of the product is confirmed by NMR.

EXAMPLE 24

Helichromic (+)-2-[6-methoxybenzothiazolylazo]-5-[4-(2-methylbutylamino)naphthylazo]-1,4-dimethylbenzene

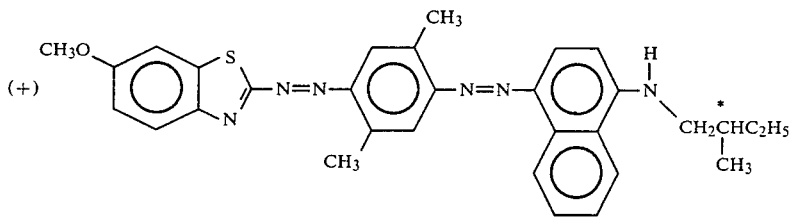

6-methoxy-2-aminobenzothiazole (5 gm) was dissolved in 120 ml dry 1,4-dioxane and the solution was warmed on a water bath to 60° C. Subsequently 4.05 ml of isoamyl nitrite, dissolved in 20 ml 1,4-dioxane was allowed to flow quickly into the reaction solution. Immediately, drop by drop, within a 25 minute period, 110 ml of a 1.5 molar sodium propanolate solution in n-propanol was added. The precipitate was filtered off with suction, digested with ether and dried. The 6-methoxybenzothiazole-2-diazotate as the monohydrate was recovered in 70% yield. The structure of the monohydrate was confirmed by NMR.

2.45 gm of the above compound was dissolved in 50 ml warm, distilled water and cooled to 10° C. 1.21 gm of 2,5-dimethyl aniline was dissolved in 100 ml glacial acetic acid. The diazotate solution was then dropped into the stirred acetic acid solution of amine. Immediately the bright red coupled product separated and an hour after the addition was completes the addition of 250 ml water separated the dye intermediate. A 20% by weight solution of sodium hydroxide in water was added until the pH was neutral (approximately 7) and the product was removed by filtration, washed with water, and dried at room temperature. The structure of the product was

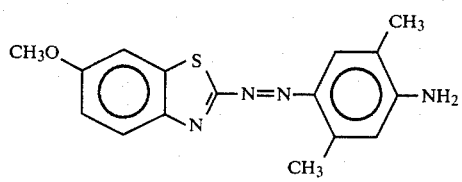

The above compound (4.56 gm) is dissolved in 40 gm of a 40% solution of nitrosylsulfuric acid, cooled to 0° C. and allowed to diazotize for 4 hours. Upon completion of the diazotization, the solution is poured into a solution of 3.4 gm (+)-N-(2-methylbutyl)-α-naphthylamine, prepared according to Example 6, in 50 ml glacial acetic acid. After allowing coupling to proceed for about 2 hours, sodium acetate is added to raise the pH to 5. Neutralization of the mixture to pH7 with a solution of 20% by weight sodium hydroxide in water, followed by filtration and water washed yields the helichromic dye. The structure of the dye is confirmed by NMR.

EXAMPLE 25

Helichromic (+)-1-(naphthylthiazolylazo)-4-[4-(2-methylbutylamino)naphthylazo]benzene

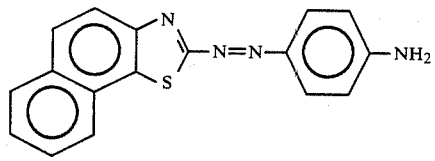

1.6 g of the above intermediate was diazotized in cold nitrosylsulfuric acid solution and coupled to one equivalent (1.74 gm) (+)-N-(2-methylbutyl)-naphthylamine, prepared according to the procedure of Example 6, which had been dissolved in 50 ml glacial acetic acid. The desired blue helichromic compound was recovered by filtration. The structure of the product was confirmed by NMR.

EXAMPLE 26

Helichromic (+)3-methylcyclohexyl dye

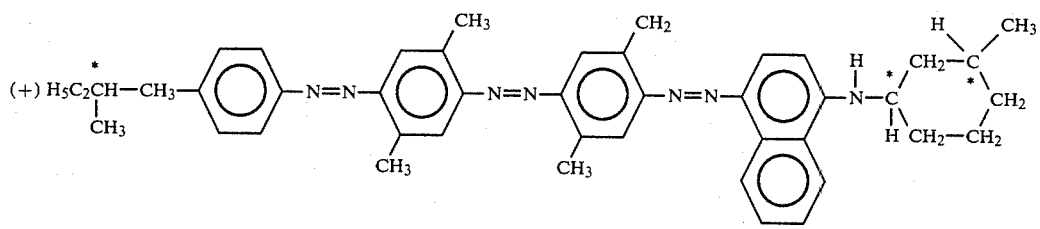

The helichromic dye intermediate (+)-p-2methylbutyl)phenylazo-[2,5]-dimethylphenylazo-[2,5]-dimethylaniline (4.27 gm), prepared according to Example 11 was dissolved in 50 ml of a solution of 50% sulfuric acid in water and cooled to 0° C. Sodium nitrite (0.69 gm) as a 20% by weight solution in water was added dropwise and stirring was continued for 4 hours. Complete diazotization occurred and the clear diazonium was poured into a solution of 50 ml glacial acetic acid

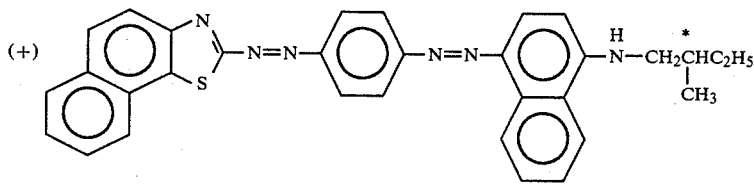

2-amino-naphtyl-[1,2]-thiazole (2.02 gm) was converted to the corresponding diazotate according to the procedure of Example 24. 2.38 gm of the diazotate was dissolved in 50 ml water at room temperature and slowly dropped into 100 ml of a 30% sulfuric acid in water solution containing 0.9 gm aniline. The coupling action occurred immediately and upon neutralization with a 30% by weight solution of sodium hydroxide in water the product was filtered and washed with water. 3 gm (90% theoretical) of the desired dye intermediate was obtained. The structure of the intermediate was containing 2.23 gm (+)-N-(-3-methylcyclohexyl)-α-napthylamine, prepared according to Example 9. Coupling was allowed to occur for 1 hour and the product was neutralized with a 20% sodium hydroxide in water solution and filtered. The dye product was purified by chromatography using silica gel and a 4:1 toluene/methanol solution as the eluent. The structure of the helichromic product was confirmed by NMR.

EXAMPLE 27

Helichromic (+)-4-[4-(2-methylbutyl)phenylazo]-4'-[4-)camphanylamino)naphthylazo]-azobenzene

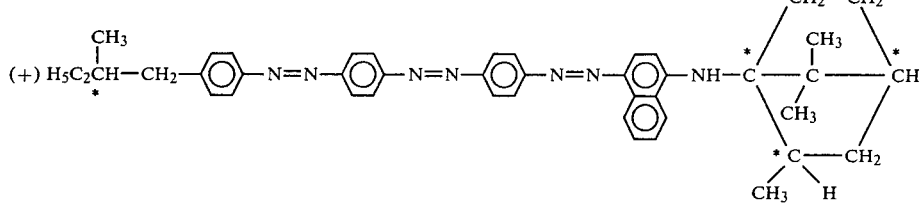

(+)-N-camphanyl-α-naphthylamine (2.26 gm), prepared according to Example 8, was dissolved in 25 ml glacial acetic acid. (+)-p-(2-methylbutyl)phenylazo(-phenylazo)aniline (0.1 mole), prepared according to Example 12, was dissolved in 50 ml 87% sulfuric acid and diazotized using 40% nitrosylsulfuric acid in water (0.1 mol) added dropwise to the amine at 5° to 10° C. After the completion of diazotization the solution of chiral α-naphthylamine in acetic acid was added to the diazo solution along with 100 gm ice. After the coupling reaction occurred (1 hour) the mixture was diluted with 100 gm water and solid sodium acetate trihydrate was added until the pH was 5. The solution was then brought to pH 7 using a solution of 20% sodium hydroxide in water. The solid dye was collected by filtration, dried and recrystallized from toluene. Chromatography on silica using dichloromethane as eluent afforded the desired helichromic compound. The structure of the helichromic dye was confirmed by NMR.

EXAMPLE 28

Helichromic (+)-1-[4-(4-methylhexyl)phenylazo]-4-[4-(2-methylbutyl)benzylidene]naphthalene

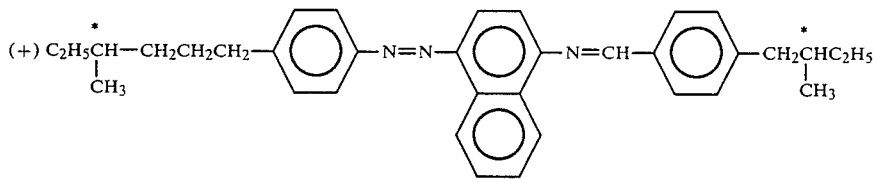

(+)4-(4-methylhexyl)aniline (18.1 gm), prepared according to Example 10, is added to a solution of 100 ml concentrated hydrochloric acid and 100 ml water. The slurry is stirred, cooled 0° C., and diazotized using 6.9 gm sodium nitrite. The clear diazonium solution is then added to a solution of 15.1 gm 1,4-diaminonaphthylene in 50 ml glacial acetic acid. Coupling occurs and the pH is adjusted to 5 by addition of solid sodium acetate trihydrate. The coupled product is recovered by neutralizing the mixture with a solution of 25% sodium hydroxide in water, and collecting the product by filtration. The product (24.7 gm) is then dissolved in 100 ml hot ethanol and 17.6 gm (+)-4-(2-methylbutyl)benzaldehyde, prepared according to Example 5, is added. To this mixture is added 0.1 gm p-toluene sulfonic acid and the dye product forms almost immediately. Upon cooling the product is collected by filtration. Chromatography on silica using toluene as eluent affords the helichromic dye. The structure of the dye is confirmed by NMR.

EXAMPLE 29

Helichromic (+)-bis-2-methylbutylphenyl-1,4-tetrazine

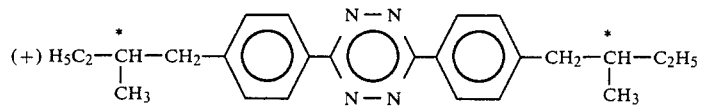

(+)-p-2-methylbutylbenzaldioxime was converted in the presence of an excess of hydrazine hydrate to an intermediate which was then oxidized using sodium nitrite, whereupon the dimer (+)-Bis-2-methylbutylphenyl-1,4-tetrazine was recovered as a red helichromic compound.

EXAMPLE 30

Helichromic (+)-2,2'(2-methylbutyl)-diphenodioxazine

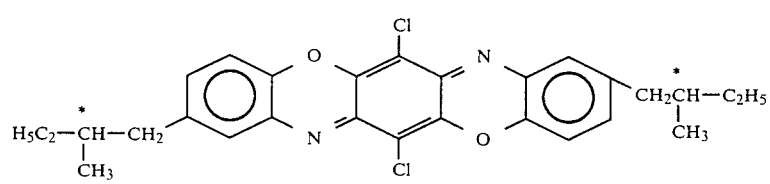

One equivalent of chloranil was refluxed with two equivalents of (+)-p-2-methylbutylaniline in the presence of an equivalent of anhydrous magnesium oxide. The intermediate compound was separated by crystallization and filtration and was oxidized by boiling in nitrobenzene containing a catalyst of phosphorus pentachloride. The helichromic compound, (+){2,2'(2-methylbutyl)}diphenodioxazine, was recovered by crystallization and subsequent chromatographic purification.

EXAMPLE 31

Helichromic (+)-4,9(bis-2-methylbutylphenylazo)carbazole

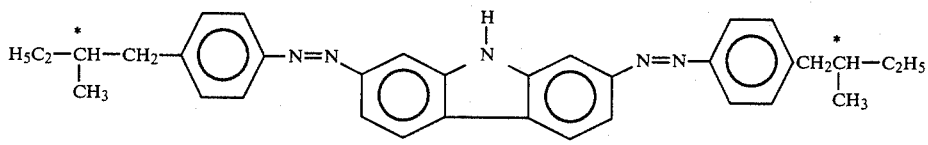

One equivalent of 2,6-diaminocarbazole was tetraazotized by the addition of 2 equivalents of sodium nitrite to a solution of the aforementioned carbozole in hydrochloric acid solution at °C. Two equivalents of (+)-p-2-methylbutylbenzene were dissolved in acetic acid solution and combined with the above carbozole tetrazonium solution with the addition of sodium acetate as a buffer. Upon the completion of the coupling reaction, the crude helichromic dye was recovered and purified by column chromatography.

EXAMPLE 32

Helichromic-smectic liquid crystal display cells were assembled as described hereinabove. The top and bottom substrates were made from two pieces of borosilicate glass, one inch by one inch square, spaced 15 micrometers apart. The bottom electrode was an aluminum coating having 0.1 ohms per square resistance. The top electrode was a 0.1 micrometer thick coating of indium-tin-oxide. The bottom substrate had a micro-lenticular surface wherein the dimples had a depth range of about 0.5 to 2.5 micrometers, and a diameter from about 10 to 20 micrometers.

Two fill mixtures were prepared to demonstrate the effect of the helichromic compounds of the present invention. One fill mixture contained smectic liquid crystal material comprising

| | % by weight |
|---|---|
| 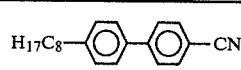 | 26.5 |
| 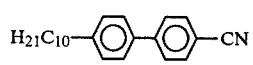 | 14.6 |
| 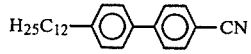 | 32.0 |
| 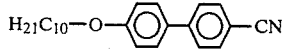 | 16.2 | and 10.7% by weight of the following liquid crystal composition

| | % by weight |
|---|---|
| 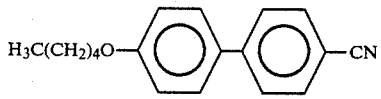 | 30% |
| 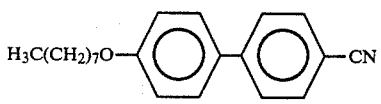 | 15% |
| 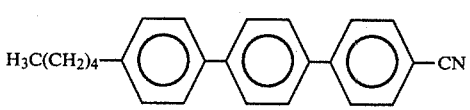 | 10% |
| 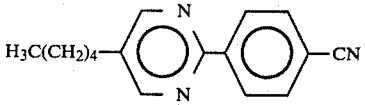 | 10% |
| 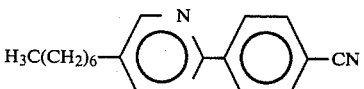 | 20% |
| 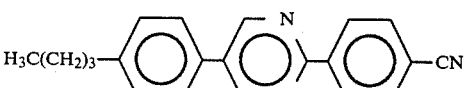 | 15% | which is commercially available as "ROTN 404" from Hoffman LaRoche. The entire liquid crystal composition described above will be referred to as "Smectic Liquid Crystal Composition A" hereinbelow. To 10 grams of Smectic Liquid Crystal Composition A was added 150 milligrams of the helichromic compound

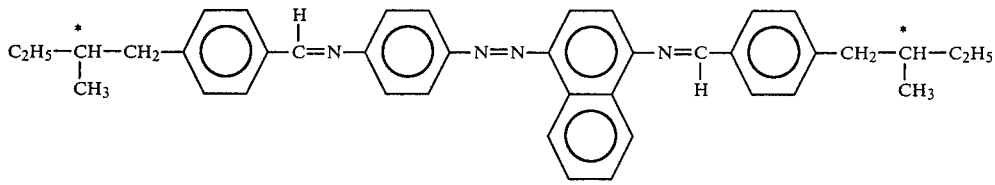

The resultant fill mixture is Fill Mixture 1.

The second fill mixture comprised 10 grams of the Smectic Liquid Crystal Composition A, described hereinabove, mixed with 7.0 percent by weight of the optically-active additive (CB-15) available from BDH Chemicals, Inc., and 150 milligrams of a racemic mixture of the pleochroic dye

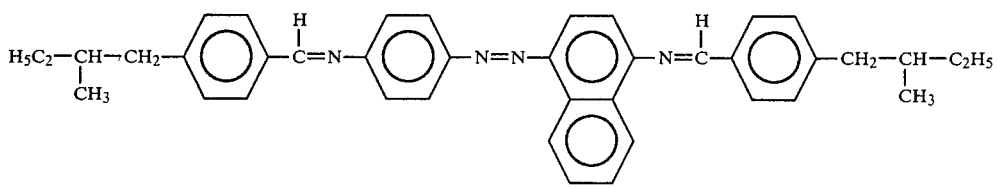

This mixture is Fill Mixture 2.

Display cells were filled with the above two fill mixtures. The optical and electrical characteristics of the cells were determined by inserting the test cells in the optical pathway of a remote sensing, high-speed computerized spectroradiometer. The spectroradiometer used was a Gamma Scientific-Tektronix Model DR-2, SC4 Digital Radiometer with RS-1 lamp controlled by a Tektronix 4052 computer.

Test cell brightness was determined in the following way. Each cell was subjected to a thermal impulse of 40 volts at 4 amperes for 6 microseconds, after which a voltage was applied to the cell in an amount sufficient to background the entire cell. The brightness of the background was measured as the amount of light reflected by the cell. Percent brightness was reported as the brightness of the cell as a percent of the brightness of a standard (Barium Oxide) white reflectance test card.

The modulation voltage for each cell was determined as follows. Electronically addressing voltages were applied to the cell electrodes as the cell was cooling from the upper thermal phase to the lower thermal phase and the brightness versus applied voltage was determined spectroradiometrically. The voltage required to attain 90 percent of maximum brightness is the modulation voltage. Contrast ratio was measured by determining the average test cell brightness (brightness of the background as described above) as a function of wavelength throughout the visible region after thermally and electronically addressing the cell and comparing that brightness to the imaged state brightness. The response time measured on the same equipment was a measurement of the length of time required to switch the cell from 10 percent of maximum brightness to 90 percent of maximum brightness.

Modulation voltage, response time, contrast ratio and percent brightness are reported in Table I below.

TABLE I

|  | Fill Mixture 1 | Fill Mixture 2 |
|---|---|---|
| Modulation Voltage (V) | 4 | 25.5 |
| Response Time (ms) | 9 | 32 |
| Contrast Ratio | 11.2 | 5.3 |
| Brightness % | 70 | 68 |

As illustrated in Table I, the helichromic device containing a helichromic compound (Fill Mixture 1) exhibited a lower modulation voltage, a faster response time, and a higher contrast ratio at about the same brightness as the display containing a corresponding optically-inactive pleochroic dye and the cholesteric dopant (CB-15) (Fill Mixture 2).

EXAMPLE 33

Display cells were assembled as in Example 32. Two fill compositions were prepared. One fill mixture (Fill Mixture 3) comprised 10 grams of Smectic Liquid Crystal Mixture A, prepared according to Example 32, in admixture with 150 mg of the helichromic compound

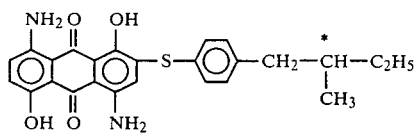

The other mixture (Fill Mixture 4) comprised 10 grams of Smectic Liquid Crystal Mixture A to which 7 percent by weight of the cholesteric dopant CB-15 had been added, and 150 milligrams of a racemic mixture of the pleochroic dye

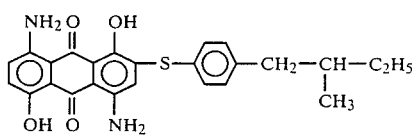

Displays were filled with the above two types of mixtures and the modulation voltage, response time, contrast ratio, and percent brightness were measured as in Example 32. The results are reported in Table II, hereinbelow.

TABLE II

|  | Fill Mixture | |
| --- | --- | --- |
|  | 3 | 4 |
| Modulation Voltage (V) | 4 | 25 |
| Response Time (ms) | 19 | 30 |
| Contrast Ratio | 14.5 | 6.26 |
| Brightness % | 70 | 71 |

The display containing Fill Mixture 3, having a helichromic compound, had a lower modulation voltage, and a faster response time with a higher contrast ratio at the same brightness as the display containing Fill Mixture 4, containing a corresponding optically-inactive pleochroic dye and a cholesteric dopant.

EXAMPLE 34

Display cells were assembled as in Example 32. Two fill compositions were prepared. One fill mixture comprised the following smectic liquid crystal composition

|  | % by weight |
| --- | --- |
| $H_{11}C_5$—⬡—C(=O)—O—⬡—O—$C_7H_{15}$ | 39.3 |
| $H_{11}C_5$—⬡—C(=O)—O—⬡—O—$C_5H_{11}$ | 27.5 |
| $H_{21}C_{10}$—⬡—⬡—CN | 33.2 |

The composition described above will be referred to as "Smectic Liquid Crystal Composition B" hereinbelow. Fill Mixture 5 comprised 10 grams of Smectic Liquid Crystal Composition B and 150 mg of the helichromic compound

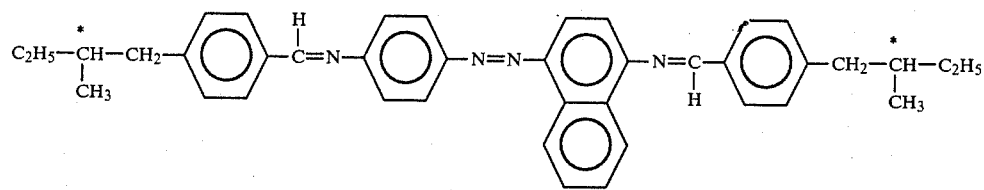

Fill Mixture 6 comprised 10 grams of Smectic Liquid Crystal Composition B described hereinabove mixed with 7.0 percent by weight of the optically-active additive (CB-15), and 150 milligrams of a racemic mixture of the pleochroic dye

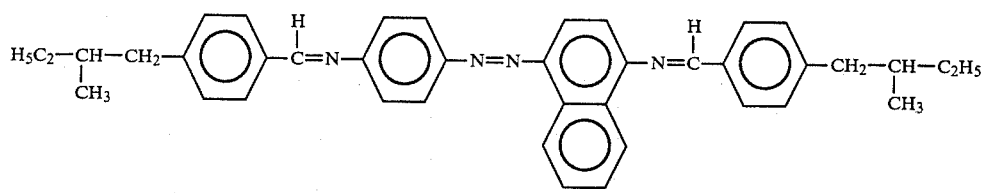

Displays were filled with Fill Mixtures 5 and 6 and the modulation voltage, response time, contrast ratio and percent brightness were measured for each type of display, as in Example 32. The results are reported in Table III hereinbelow.

TABLE III

|  | Fill Mixture | |
| --- | --- | --- |
|  | 5 | 6 |
| Modulation Voltage (V) | 6 | 27 |
| Response Time (ms) | 7 | 55 |
| Contrast Ratio | 10.8 | 5.3 |
| Brightness % | 72 | 70 |

Again, Table III illustrates that the helichromic device containing a helichromic compound (Fill Mixture 5) has a lower modulation voltage, a faster response time, and a higher contrast ratio at about the same brightness as the display containing a corresponding optically-inactive pleochroic dye and CB-15.

EXAMPLE 35

Display cells were assembled as in Example 32. Two fill compositions were prepared. One fill mixture (Fill Mixture 7) comprised 10 grams of Smectic Liquid Crystal Mixture B, prepared according to Example 34, in admixture with 150 mg of the helichromic compound

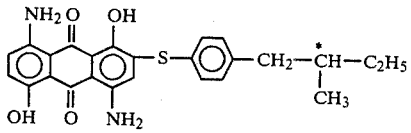

The other fill mixture, Fill Mixture 8, comprised 10 grams of Smectic Liquid Crystal Mixture B to which 7 percent by weight of the cholesteric dopant CB-15 had been added, and 150 milligrams of a racemic mixture of the pleochroic dye

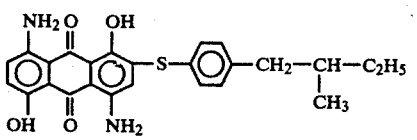

Displays were filled with Fill Mixtures 7 and 8, and the modulation voltage, response time, contrast ratio and percent brightness were measured for each type of display, as in Example 32. The results are reported in Table IV hereinbelow.

TABLE IV

|  | Fill Mixture | |
| --- | --- | --- |
|  | 7 | 8 |
| Modulation Voltage (V) | 6 | 25 |
| Response Time (ms) | 16 | 65 |
| Contrast Ratio | 16.2 | 6.2 |
| Brightness % | 72 | 70 |

Again, Table IV illustrates that the helichromic device containing a helichromic compound (Fill Mixture 7) has a lower modulation voltage, a faster response time, and a higher contrast ratio at about the same brightness as the display containing a corresponding optically-inactive pleochroic dye and CB-15.

What we claim is:

1. A composition consisting essentially of a smectic liquid crystal material, and, in admixture therewith, an organic, nonionic, nonliquid-crystalline helichromic compound, said helichromic compound being soluble in said smectic liquid crystal material, said helichromic compound being a circularly dichroic dye, and said helichromic compound having the general formula Q(̵Z)$_n$ wherein Q is an organic group having a chromophoric character;

Z is an optically-active organic group; and n is an integer having a value of 1 or greater.

2. The composition of claim 1 wherein said Z comprises an asymmetric carbon atom.

3. The composition of claim 1 wherein Z is selected from the group consisting of (+)-2-methylalkyl, (+)-3-methylalkyl, (+)-2-methylalkoxy, (+)-3-methylalkoxy, (+)-citronellyl, (+)-camphanyl, (+)-3-methylcyclohexyl, (+)-α-methylbenzyl, (+)-2-methylbutylbiphenyl, (+)-2-methylbutylphenylthio, (+)-3-ethylhexylphenylbenzoate, (+)-2-methylbutylmethyl-2,3-dihydropermidine, (+)-3-methylcyclopentyl-2,3-dihydropermidine, (+)-2-methylcyclohexyl-2,3-dihydropermidine, (+)-2-phenethylamine, and (+)-N-2-methylbutylaminonapthalene.

4. The composition of claim 1 wherein Q is a radical selected from the group consisting of azo, azo-stilbene, benzothiazolyl polyazo, methine, azo-methine, merocyanine, methine-arylidene, tetrazine, oxadiazine and carbozole-azo radicals.

5. The composition of claim 1 wherein Q is an anthraquinone radical and Z is substituted in one or more of the 1 through 8 positions of said anthraquinone radical.

6. The composition of claim 5 wherein n is an integer having a value between 1 and 4 and Z is substituted in the 2, 3, 6 or 7 positions of said anthraquinone radical, or combinations thereof.

7. The composition of claim 1 wherein Q is an anthraquinone heterocyclic dicarboximide radical and Z is substituted on the nitrogen of said heterocyclic dicarboximide radical.

8. The composition of claim 3 wherein Z additionally comprises an organic linking group, said linking group selected from the group consisting of —CH=N—, —CH=CH—, —C=C, —N=N—, —NH—, —N(alk)—, —O—, —S—, (̵CH$_2$)̵$_p$, —O(̵CH$_2$)̵$_p$,

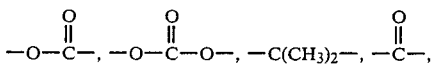

—C$_6$H$_{10}$— phenyl groups, naphthyl groups, cyclic carboximide groups and combinations thereof, wherein p is 1, 2, 3, 4 or 5.

9. The composition of claim 1 wherein Q additionally comprises one or more ballasting groups selected from the group consisting of —NH$_2$, (̵CH$_2$)̵$_p$CH$_3$, —O—(CH$_2$)̵$_p$CH$_3$, —CH(CH$_3$)$_2$,

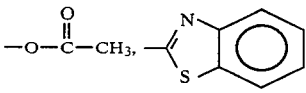

C$_6$H$_{11}$, phenyl groups, naphthyl groups, heterocyclic nitrogen, oxygen and sulfur-containing rings and combinations thereof, wherein p is 0, 1, 2, 3 or 4.

10. The composition of claim 1 wherein Q comprises at least one aromatic ring having one or more auxochromic substituents independently selected from the group consisting of lower alkyl, lower alkoxy, F, Cl, Br, NO$_2$, NH$_2$, N(alk)$_2$, —N=CH(alk), OH, CN, CF$_3$, SCN, OCH$_3$, SH and carbonyl groups substituted thereon.

11. The composition of claim 1 wherein said helichromic compound is selected from the group consisting of

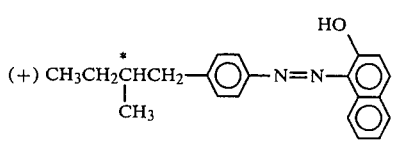

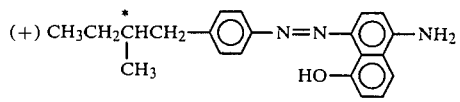

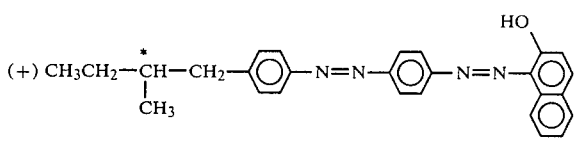

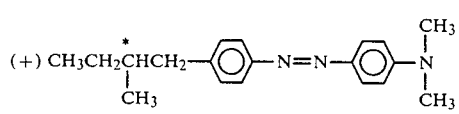

-continued
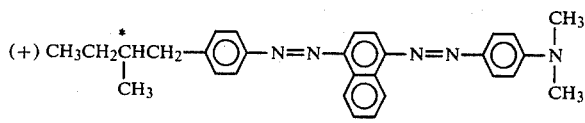
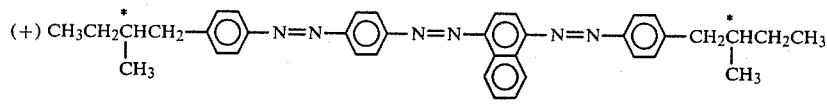
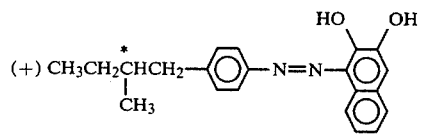 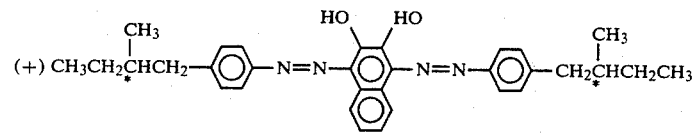
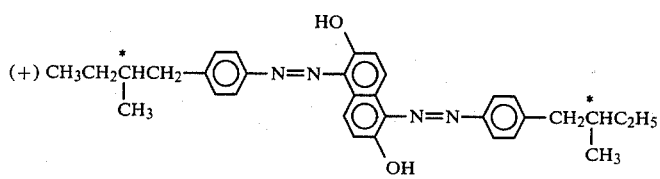
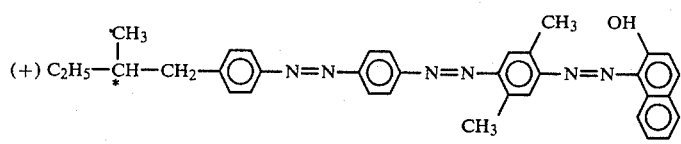
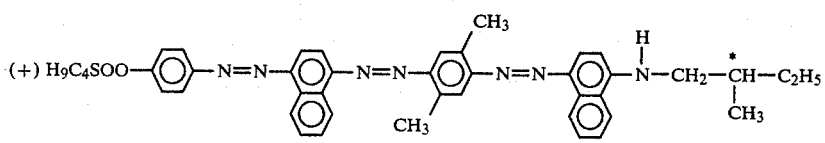
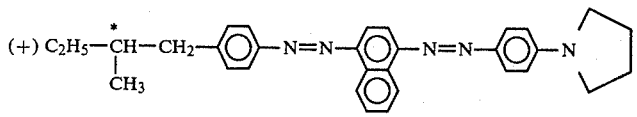
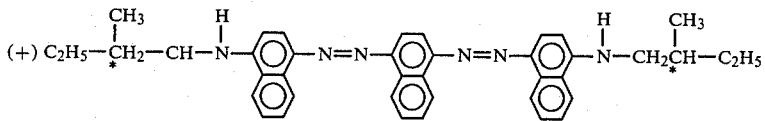
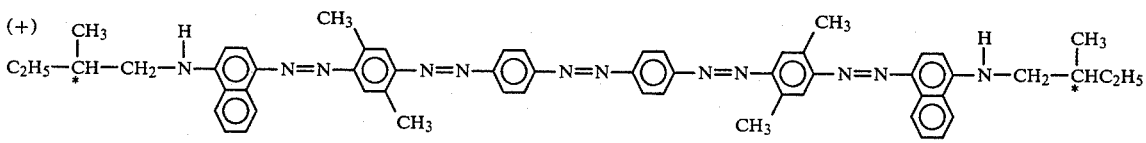

-continued
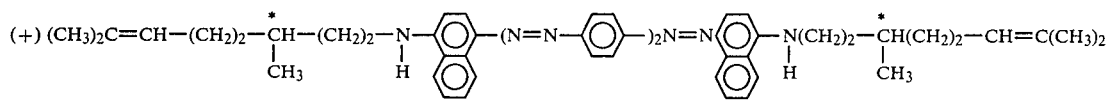
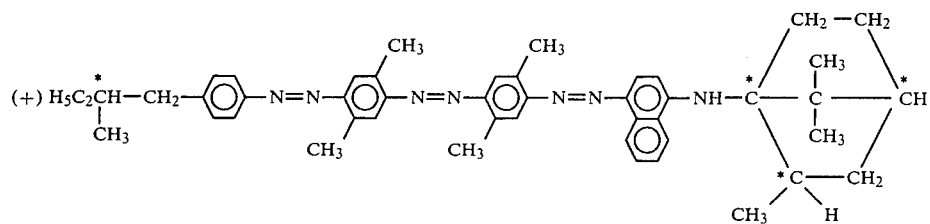
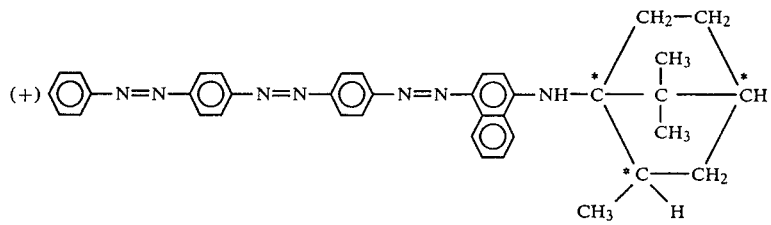
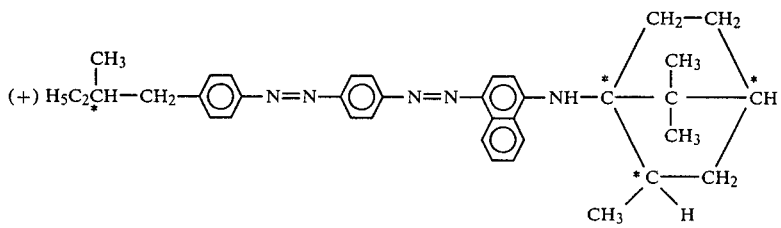
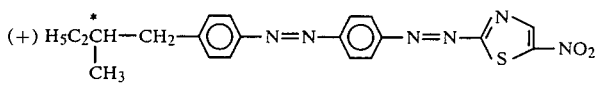  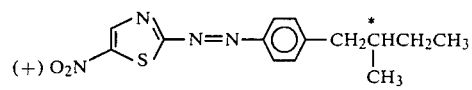
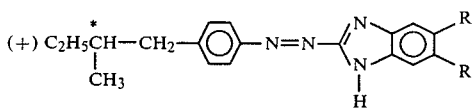  and  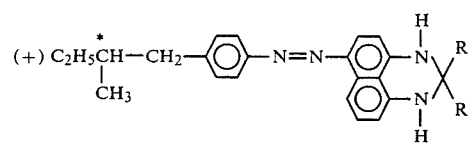
R = lower alkyl (C$_1$–C$_4$)
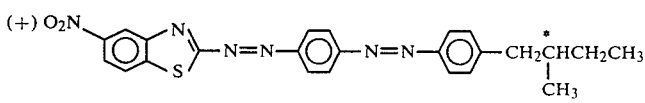
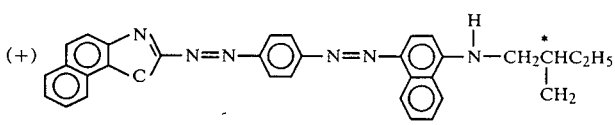

-continued
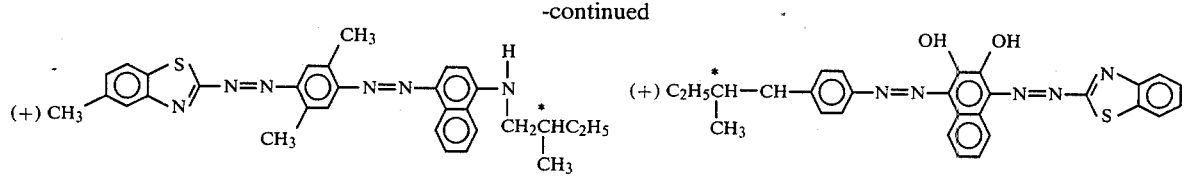
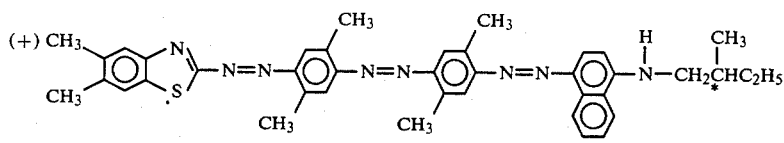
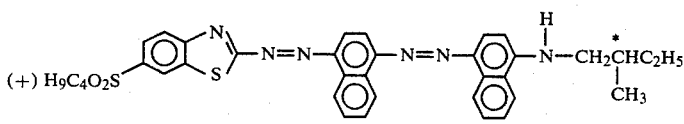
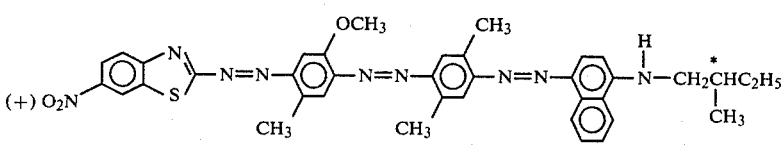
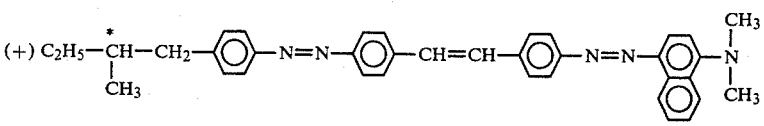
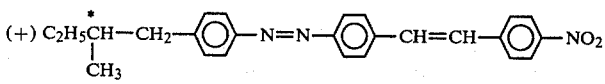
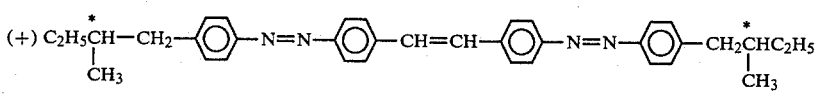
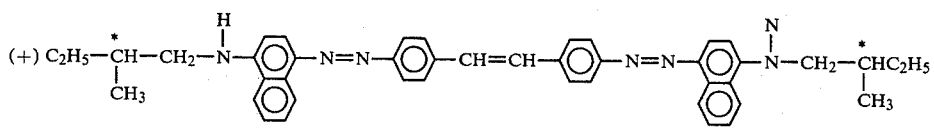
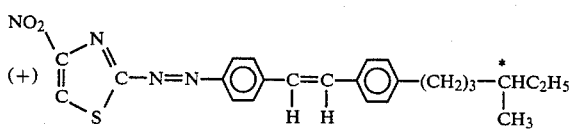
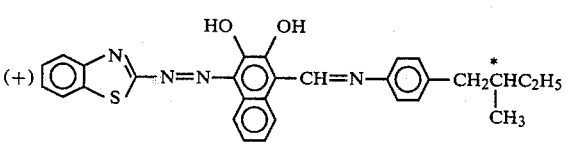

-continued
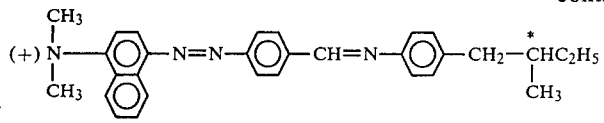
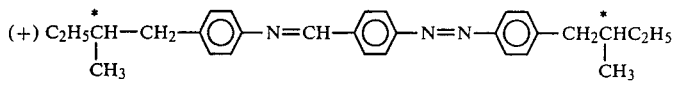
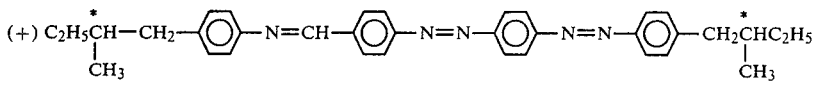
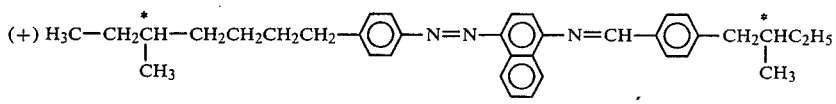
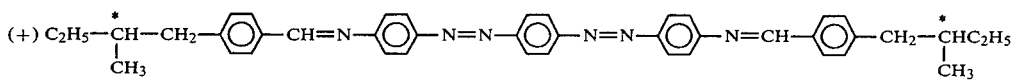
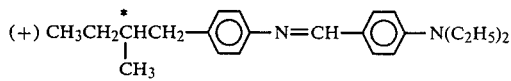
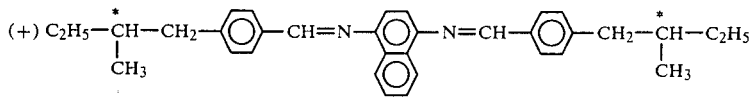
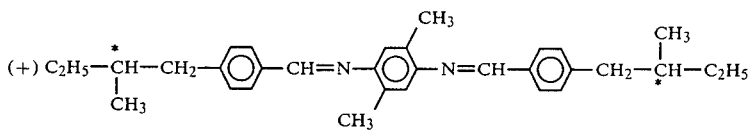
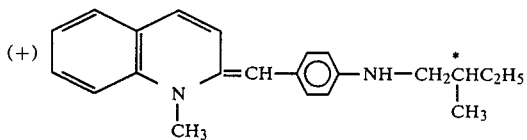
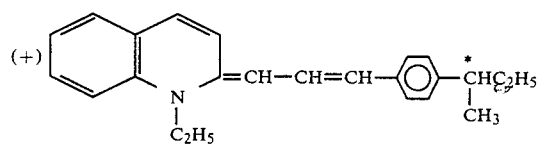
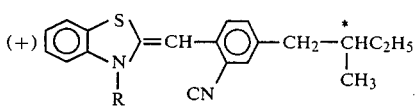
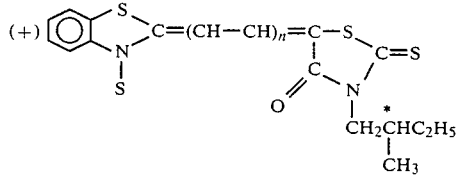
n = 1, 2 or 3.

-continued
(+) 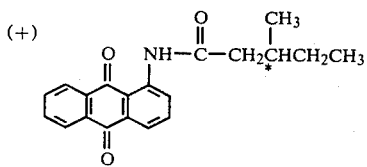
(+) 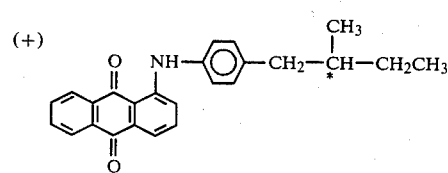
(+) 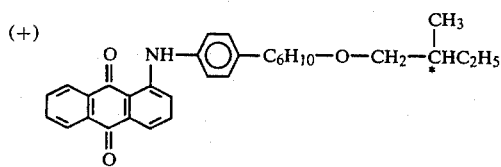
(+) 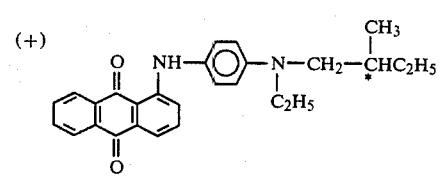
(+) 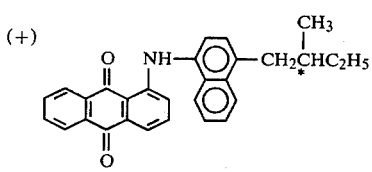
(+) 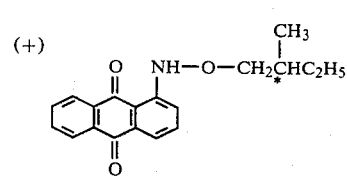
(+) 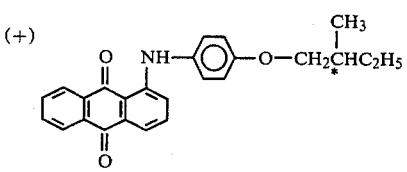
(+) 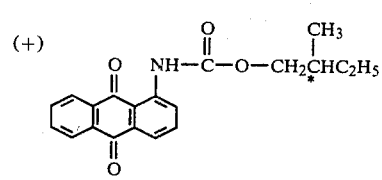
(+) 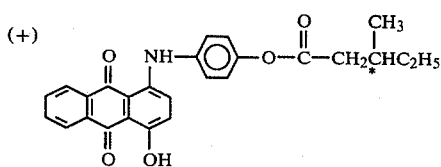
(+) 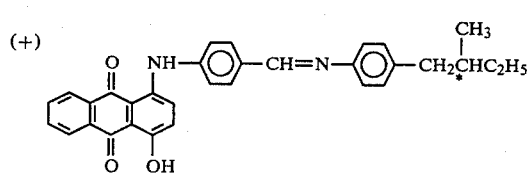
(+) 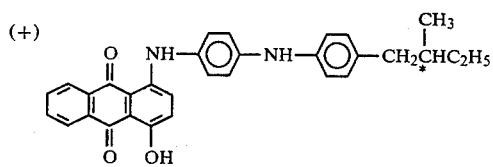
(+) 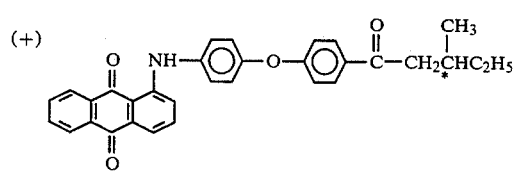
(+) 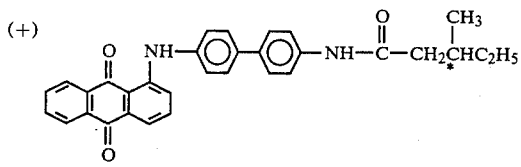
(+) 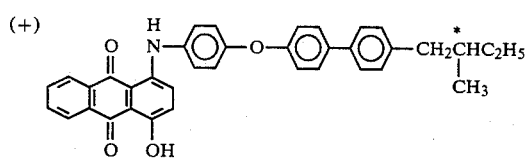

71 72
-continued
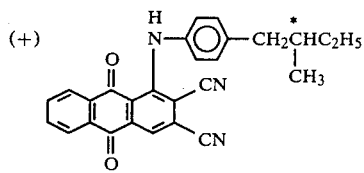
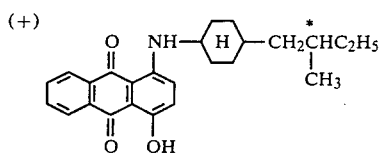
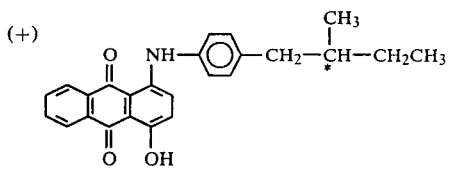
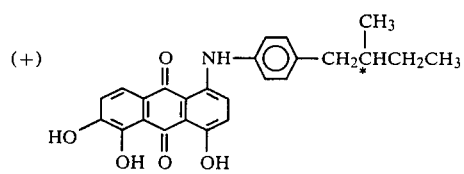
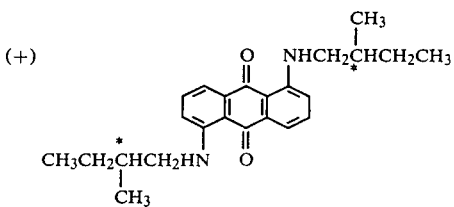
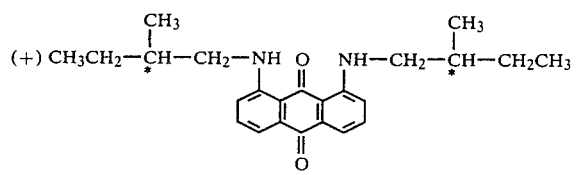
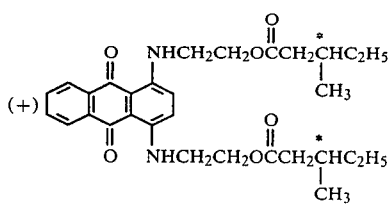
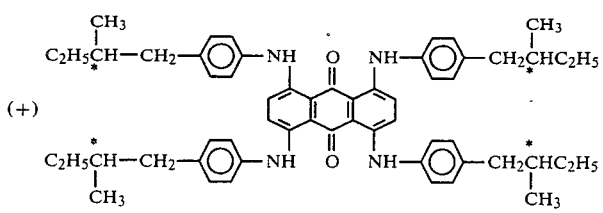
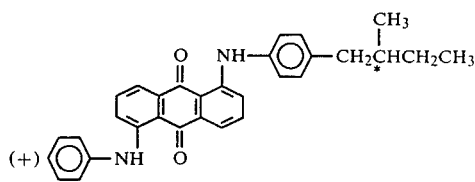
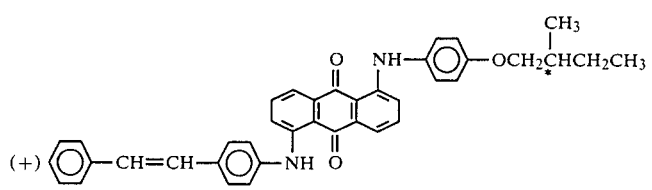
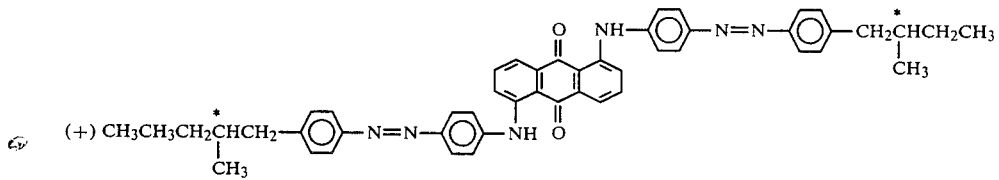
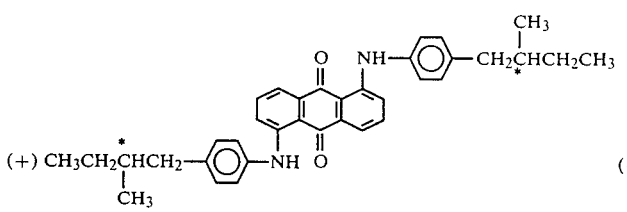
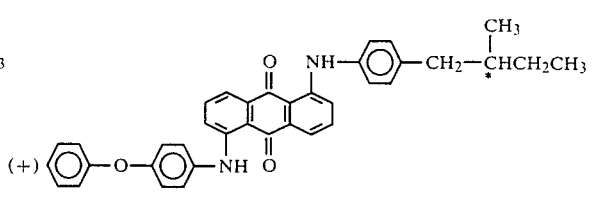
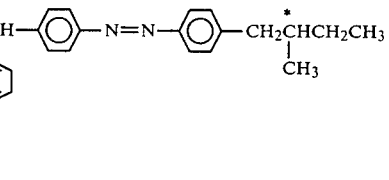

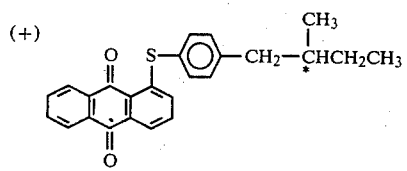
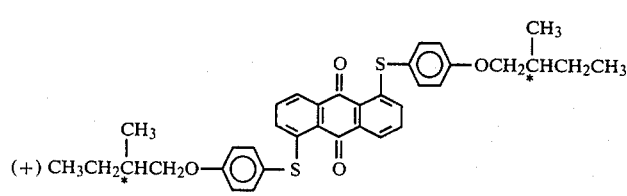
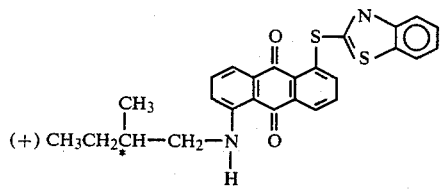
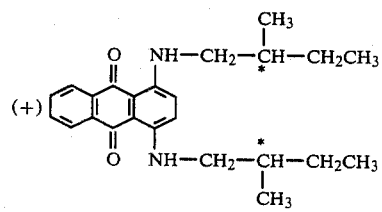
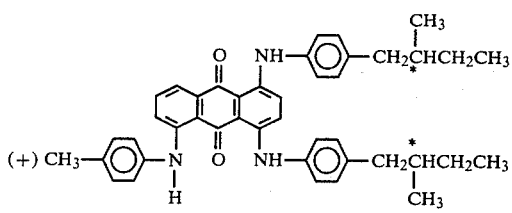
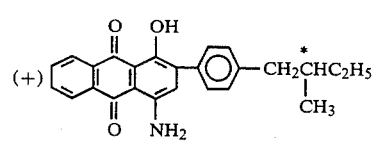
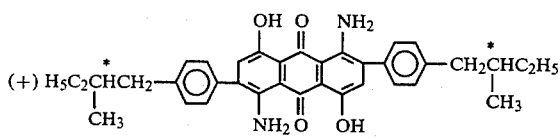
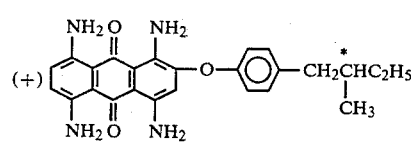
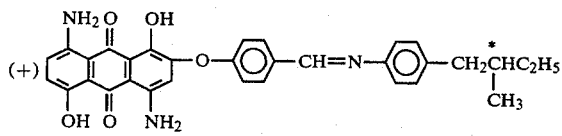
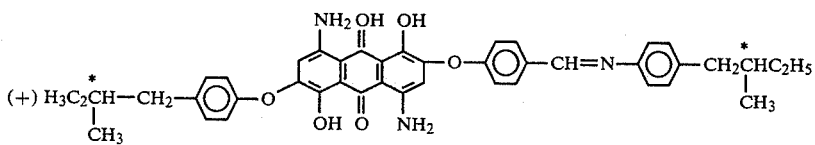
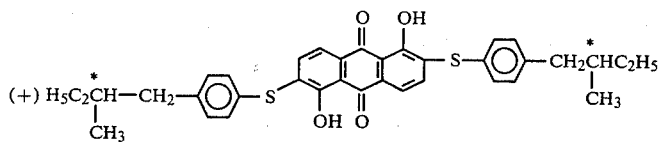
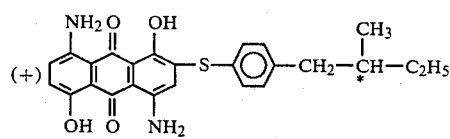
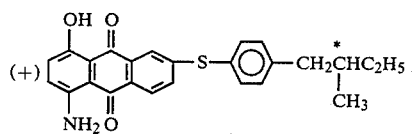
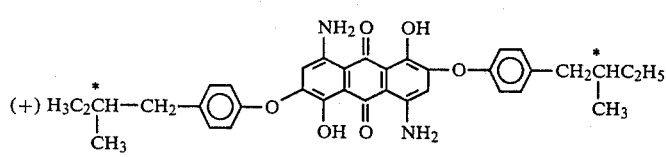

-continued
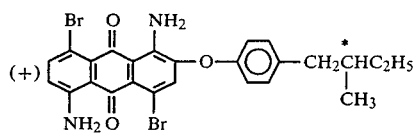
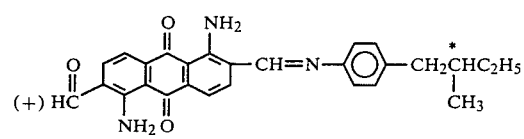
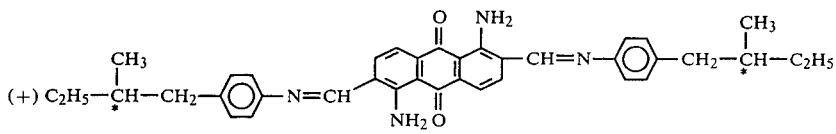
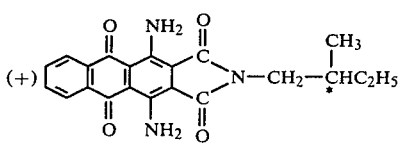
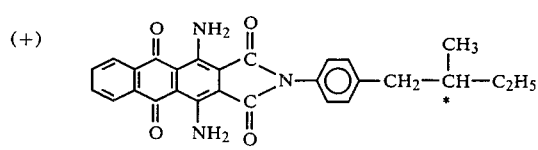
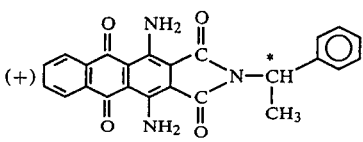
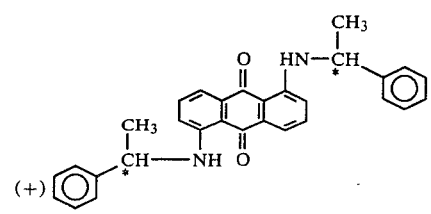
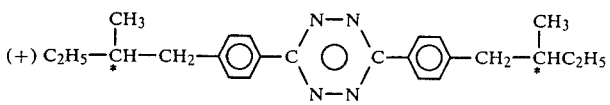
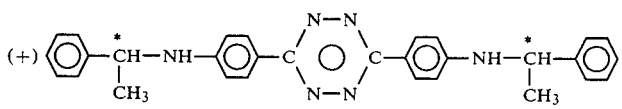
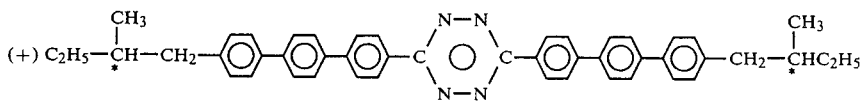
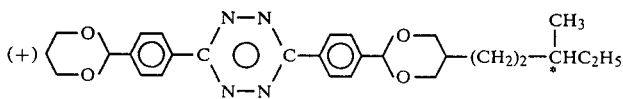
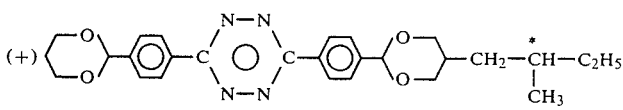

-continued

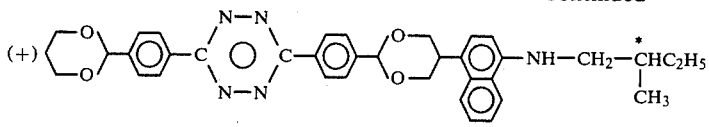

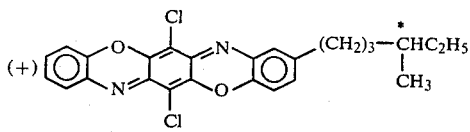

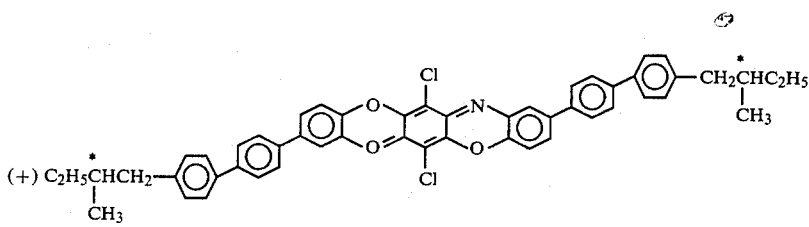

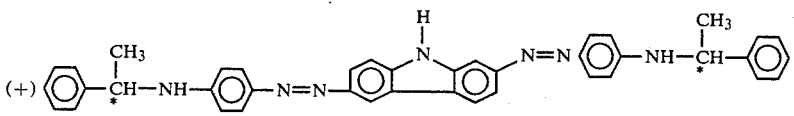

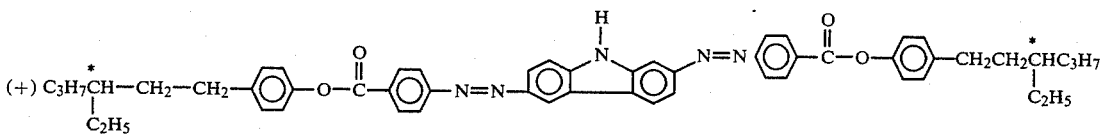

12. The composition of claim 1 wherein said helichromic compound is present in an amount effective to provide said composition with the ability to propagate incident light in a circularly polarized manner, so that all polarizations of said light are absorbed when said composition is used in a helichromic-smectic liquid crystal display device.

13. The composition of claim 12 wherein said helichromic compound is present in a concentration of between about 0.1 and 5 percent by weight of said smectic liquid crystal material.

14. The composition of claim 1 wherein said smectic liquid crystal material is selected from the group consisting of smectic A and smectic C liquid crystal materials.

15. The composition of claim 14 wherein said smectic liquid crystal material is selected from the group consisting of alkyl and alkoxy substituted cyano diphenyls and esters of alkyl and alkoxy substituted cyano diphenyls.

16. A thermally addressable liquid crystal display device having no auxiliary polarizers, which provides a high contrast image against a background comprising:
a layer of a composition consisting essentially of a liquid crystal medium in admixture with an organic, nonionic, nonliquid-crystalline helichromic compound, said layer disposed between a top substrate and a bottom substrate, said helichromic compound being soluble in said liquid crystal medium, said helichromic compound being a circularly dichroic dye, and said helichromic compound having the general formula Q(Z)$_n$ wherein
Q is an organic group having a chromophoric character;
Z is an optically-active organic group; and
n is an integer having a value of 1 or greater;
said liquid crystal medium being thermally sensitive and having a transition between at least two thermal phases, an upper phase being a nematic phase and a lower thermal phase being a smectic phase, said mixture having two possible states of orientation in said smectic phase, a first orientation state being substantially light absorbing and a second state being substantially light transmissive;
a means of affecting a thermal transition between said lower thermal phase and said upper thermal phase; and
a means of electrically addressing portions of said mixture to develop said second light transmissive state when said mixture passes rapidly into said lower thermal state from said upper thermal state, the remaining unaddressed portions of said mixture developing said first substantially light absorbing state when said mixture passes rapidly into said lower thermal state from said upper thermal state.

17. The display device of claim 16 wherein said means of electrically addressing portions of said medium comprises at least one electrode disposed adjacent said medium.

18. The display device of claim 17 wherein said electrode comprises a transparent electrically-conductive material which is disposed between said top substrate and said medium, said top substrate comprised of a transparent material.

19. The display device of claim 18 wherein said means of affecting a thermal transition between said lower thermal phase and said upper thermal phase comprises at least one heating electrode disposed between said bottom substrate and said medium.

20. The display device of claim 19 wherein said device additionally comprises a thermal barrier layer disposed between said heating electrode and said bottom substrate, said liquid crystal medium thus capable of absorbing a substantial amount of the heat from said heating electrode due to the insulative character of said thermal barrier layer.

21. The display device of claim 20 wherein said thermal barrier layer comprises polymonochloro-paraxylylene.

22. The display device of claim 16 wherein said device additionally comprises means disposed between said bottom substrate and said medium for reflecting light passing through said medium.

23. The display device of claim 22 wherein said means for reflecting said light and said means for affecting a thermal transition between said lower thermal phase and said upper thermal phase are comprised in at least one reflective heating electrode.

24. The display device of claim 23 wherein said reflective heating electrode has a micro-lenticular surface of concave or convex shaped cavities having a depth range of from about 0.5 to 2.5 micrometers and a diameter ranging from about 10 to 20 micrometers.

25. The display device of claim 22 wherein said device additionally comprises a light transparent material disposed adjacent said medium, between said medium and said top substrate, said light transparent material having an index of refraction equal to or less than about 1.6.

26. The display device of claim 16 wherein said means of electrically addressing portions of said medium comprises a number of column electrodes disposed between said medium and said top substrate, and said means of affecting a thermal transition comprises a number of row heating electrodes disposed between said medium and said bottom substrate, said column electrodes being substantially at right angles to said row electrodes, and said column electrodes capable of applying voltages sequentially to portions of said medium.

* * * * *